US008882763B2

(12) United States Patent
Stevenson et al.

(10) Patent No.: US 8,882,763 B2
(45) Date of Patent: Nov. 11, 2014

(54) PATIENT ATTACHED BONDING STRAP FOR ENERGY DISSIPATION FROM A PROBE OR A CATHETER DURING MAGNETIC RESONANCE IMAGING

(75) Inventors: Robert A. Stevenson, Canyon Country, CA (US); Christina A. Frysz, Orchard Park, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/535,029

(22) Filed: Jun. 27, 2012

(65) Prior Publication Data
US 2012/0265045 A1 Oct. 18, 2012

(51) Int. Cl.
| *A61B 18/14* | (2006.01) |
| *A61B 18/16* | (2006.01) |
| *A61B 5/00* | (2006.01) |
| *B82Y 30/00* | (2011.01) |
| *A61B 5/042* | (2006.01) |
| *A61B 5/055* | (2006.01) |
| *A61B 18/00* | (2006.01) |
| *A61B 19/00* | (2006.01) |
| *A61N 1/14* | (2006.01) |
| *A61N 1/08* | (2006.01) |

(52) U.S. Cl.
CPC ............... *A61B 18/16* (2013.01); *A61B 5/6852* (2013.01); *B82Y 30/00* (2013.01); *A61B 5/0422* (2013.01); *A61B 5/055* (2013.01); *A61B 5/6869* (2013.01); *A61B 5/7217* (2013.01); *A61B 18/1492* (2013.01); *A61B 2018/00839* (2013.01); *A61B 2019/5236* (2013.01); *A61N 1/14* (2013.01); *A61N 2001/086* (2013.01); *A61B 2018/00541* (2013.01)
USPC ......................................................... 606/41

(58) Field of Classification Search
CPC ..................... A61B 18/12; A61B 2018/00172; A61B 2018/00178; A61B 2018/0091; A61B 2018/1293
USPC .......................... 600/411, 421; 606/1, 41, 35
See application file for complete search history.

(56) References Cited

U.S. PATENT DOCUMENTS

| 4,188,598 A | 2/1980 | Hunt |
| 4,295,467 A | 10/1981 | Mann et al. |

(Continued)

FOREIGN PATENT DOCUMENTS

| EP | 466 424 A1 | 1/1992 |
| EP | 557 127 A2 | 8/1993 |

(Continued)

OTHER PUBLICATIONS

Roger Christoph Luchinger, "Safety Aspects of Cardiac Pacemakers in Magnetic Resonance Imaging," a dissertation submitted to the Swiss Federal Institute of Technology Zurich, 2002, Zurich.

(Continued)

*Primary Examiner* — Ronald Hupczey, Jr.
(74) *Attorney, Agent, or Firm* — Michael F. Scalise

(57) ABSTRACT

A probe or catheter to patient RF coupling for magnetic resonance imaging includes a conductive grounding strap. The strap includes a first end spaced apart from a second end, the first end configured to be permanently or removably connectable to a conductive probe or catheter housing or a conductive probe or catheter interface of a probe or catheter. A conductive patient interface is configured to be removably connectable to a portion of a patient's body and electrically conductive between the conductive grounding strap and the patient's body. The conductive patient interface is attached at the second end of the conductive grounding strap and electrically coupled to the conductive probe or catheter housing or the conductive probe or catheter interface. An electrical circuit is formed between the patient's body, the conductive patient interface, the conductive grounding strap, and the conductive probe or catheter housing or interface.

44 Claims, 14 Drawing Sheets

(56) References Cited

U.S. PATENT DOCUMENTS

| | | | |
|---|---|---|---|
| 4,320,763 A | 3/1982 | Money | |
| 4,424,551 A | 1/1984 | Stevenson et al. | |
| 4,431,005 A | 2/1984 | McCormick | |
| 4,445,501 A | 5/1984 | Bresler | |
| 4,572,198 A * | 2/1986 | Codrington | 600/410 |
| 4,643,186 A | 2/1987 | Rosen et al. | |
| 4,672,972 A | 6/1987 | Berke | |
| 4,754,752 A | 7/1988 | Ginsburg et al. | |
| 4,757,820 A | 7/1988 | Itoh | |
| 4,766,381 A | 8/1988 | Conturo et al. | |
| 4,813,429 A | 3/1989 | Eshel et al. | |
| 4,823,812 A | 4/1989 | Eshel et al. | |
| 4,832,023 A | 5/1989 | Murphy-Chutorian et al. | |
| 4,859,950 A | 8/1989 | Keren | |
| 4,932,411 A | 6/1990 | Fritschy et al. | |
| 4,960,106 A | 10/1990 | Kubokawa | |
| 4,989,608 A | 2/1991 | Ratner | |
| 5,019,075 A | 5/1991 | Spears et al. | |
| 5,095,911 A | 3/1992 | Pomeranz | |
| 5,099,208 A | 3/1992 | Fitzpatrick et al. | |
| 5,167,233 A | 12/1992 | Eberle et al. | |
| 5,178,618 A | 1/1993 | Kandarpa | |
| 5,190,046 A | 3/1993 | Sharman | |
| 5,197,468 A | 3/1993 | Proctor et al. | |
| 5,211,165 A | 5/1993 | Dumoulin et al. | |
| 5,217,010 A | 6/1993 | Tsitlik et al. | |
| 5,251,120 A | 10/1993 | Smith | |
| 5,271,400 A | 12/1993 | Dumoulin et al. | |
| 5,307,808 A | 5/1994 | Dumoulin et al. | |
| 5,307,814 A | 5/1994 | Kressel et al. | |
| 5,318,025 A | 6/1994 | Dumoulin et al. | |
| 5,323,776 A | 6/1994 | Blakeley et al. | |
| 5,323,778 A | 6/1994 | Kandarpa et al. | |
| 5,333,095 A | 7/1994 | Stevenson et al. | |
| 5,334,045 A | 8/1994 | Cappa et al. | |
| 5,334,193 A | 8/1994 | Nardella | |
| 5,348,010 A | 9/1994 | Schnall et al. | |
| 5,352,979 A | 10/1994 | Conturo | |
| 5,358,515 A | 10/1994 | Hurter et al. | |
| 5,365,928 A | 11/1994 | Rhinehart et al. | |
| 5,370,644 A | 12/1994 | Langberg | |
| 5,400,787 A | 3/1995 | Marandos | |
| 5,413,104 A | 5/1995 | Buijs et al. | |
| 5,419,325 A | 5/1995 | Dumoulin et al. | |
| 5,433,717 A | 7/1995 | Rubinsky et al. | |
| 5,437,277 A | 8/1995 | Dumoulin et al. | |
| 5,443,066 A | 8/1995 | Dumoulin et al. | |
| 5,443,489 A | 8/1995 | Ben-Haim | |
| 5,447,156 A | 9/1995 | Dumoulin et al. | |
| 5,451,232 A | 9/1995 | Rhinehart et al. | |
| 5,462,055 A | 10/1995 | Casey et al. | |
| 5,476,095 A | 12/1995 | Schnall et al. | |
| 5,498,261 A | 3/1996 | Strul | |
| 5,507,743 A | 4/1996 | Edwards et al. | |
| 5,512,825 A | 4/1996 | Atalar et al. | |
| 5,540,679 A | 7/1996 | Fram et al. | |
| 5,558,093 A | 9/1996 | Pomeranz | |
| 5,578,008 A | 11/1996 | Hara | |
| 5,588,432 A | 12/1996 | Crowley | |
| 5,590,657 A | 1/1997 | Cain et al. | |
| 5,591,218 A | 1/1997 | Jacobson | |
| 5,623,241 A | 4/1997 | Minkoff | |
| 5,662,108 A | 9/1997 | Budd et al. | |
| 5,682,897 A | 11/1997 | Pomeranz | |
| 5,685,878 A | 11/1997 | Falwell et al. | |
| 5,699,801 A | 12/1997 | Atalar et al. | |
| 5,706,810 A | 1/1998 | Rubinsky et al. | |
| 5,715,825 A | 2/1998 | Crowley | |
| 5,735,887 A | 4/1998 | Barreras et al. | |
| 5,769,800 A | 6/1998 | Gelfand et al. | |
| 5,772,693 A | 6/1998 | Brownlee | |
| 5,775,338 A | 7/1998 | Hastings | |
| 5,779,669 A | 7/1998 | Haissaguerre et al. | |
| 5,792,055 A | 8/1998 | McKinnon | |
| 5,824,029 A | 10/1998 | Weijand et al. | |
| 5,833,608 A | 11/1998 | Acker | |
| 5,840,031 A | 11/1998 | Crowley | |
| 5,864,234 A | 1/1999 | Ludeke | |
| 5,868,674 A | 2/1999 | Glowinski et al. | |
| 5,879,347 A | 3/1999 | Saadat | |
| 5,891,134 A | 4/1999 | Goble et al. | |
| 5,916,162 A | 6/1999 | Snelten et al. | |
| 5,928,145 A | 7/1999 | Ocali et al. | |
| 5,928,159 A | 7/1999 | Eggers et al. | |
| 5,938,609 A | 8/1999 | Pomeranz | |
| 5,938,692 A | 8/1999 | Rudie | |
| 5,964,705 A | 10/1999 | Truwit et al. | |
| 6,004,269 A | 12/1999 | Crowley et al. | |
| 6,011,995 A | 1/2000 | Guglielmi et al. | |
| 6,026,316 A | 2/2000 | Kucharczyk et al. | |
| 6,027,500 A | 2/2000 | Buckles et al. | |
| 6,031,375 A | 2/2000 | Atalar et al. | |
| 6,045,532 A | 4/2000 | Eggers et al. | |
| 6,066,136 A | 5/2000 | Geistert | |
| 6,099,524 A | 8/2000 | Lipson et al. | |
| 6,128,522 A | 10/2000 | Acker et al. | |
| 6,129,670 A | 10/2000 | Burdette et al. | |
| 6,171,240 B1 | 1/2001 | Young et al. | |
| 6,171,241 B1 | 1/2001 | McVeigh et al. | |
| 6,188,219 B1 | 2/2001 | Reeder et al. | |
| 6,226,545 B1 | 5/2001 | Gilderdale | |
| 6,246,896 B1 * | 6/2001 | Dumoulin et al. | 600/411 |
| 6,263,229 B1 | 7/2001 | Atalar et al. | |
| 6,272,370 B1 | 8/2001 | Gillies et al. | |
| 6,284,971 B1 | 9/2001 | Atalar et al. | |
| 6,332,089 B1 | 12/2001 | Acker et al. | |
| 6,370,427 B1 | 4/2002 | Alt et al. | |
| 6,390,996 B1 | 5/2002 | Halperin et al. | |
| 6,408,202 B1 | 6/2002 | Lima et al. | |
| 6,428,537 B1 | 8/2002 | Swanson et al. | |
| 6,539,261 B2 | 3/2003 | Dal Molin | |
| 6,549,800 B1 | 4/2003 | Atalar et al. | |
| 6,556,009 B2 | 4/2003 | Kellman et al. | |
| 6,593,884 B1 | 7/2003 | Gilboae et al. | |
| 6,606,513 B2 | 8/2003 | Lardo et al. | |
| 6,628,980 B2 | 9/2003 | Atalar et al. | |
| 6,633,780 B1 | 10/2003 | Berger et al. | |
| 6,654,628 B1 | 11/2003 | Silber et al. | |
| 6,675,033 B1 | 1/2004 | Lardo et al. | |
| 6,690,963 B2 | 2/2004 | Ben-Haim et al. | |
| 6,701,176 B1 * | 3/2004 | Halperin et al. | 600/411 |
| 6,714,809 B2 | 3/2004 | Lee et al. | |
| 6,759,388 B1 | 7/2004 | Marchant et al. | |
| 6,765,779 B2 | 7/2004 | Stevenson et al. | |
| 6,771,067 B2 | 8/2004 | Kellman et al. | |
| 6,829,509 B1 | 12/2004 | MacDonald et al. | |
| 6,871,091 B2 | 3/2005 | Wilkinson et al. | |
| 6,898,454 B2 | 5/2005 | Atalar et al. | |
| 6,901,292 B2 | 5/2005 | Hrdlicka et al. | |
| 6,904,307 B2 * | 6/2005 | Karmarkar et al. | 600/423 |
| 6,944,489 B2 | 9/2005 | Zeijlemaker et al. | |
| 6,985,775 B2 | 1/2006 | Reinke et al. | |
| 7,149,773 B2 | 12/2006 | Haller et al. | |
| 7,155,271 B2 | 12/2006 | Halperin et al. | |
| 7,174,219 B2 | 2/2007 | Wahlstrand et al. | |
| 7,236,816 B2 | 6/2007 | Kumar et al. | |
| 7,276,474 B2 | 10/2007 | Marchant et al. | |
| 7,319,905 B1 | 1/2008 | Morgan et al. | |
| 7,363,090 B2 | 4/2008 | Halperin | |
| 7,422,568 B2 | 9/2008 | Yang et al. | |
| 7,473,145 B2 * | 1/2009 | Ehr et al. | 439/729 |
| 7,966,075 B2 * | 6/2011 | Johnson et al. | 607/63 |
| 2002/0055678 A1 | 5/2002 | Scott et al. | |
| 2002/0095197 A1 | 7/2002 | Lardo et al. | |
| 2002/0192688 A1 | 12/2002 | Yang et al. | |
| 2003/0028095 A1 | 2/2003 | Tulley et al. | |
| 2003/0050557 A1 | 3/2003 | Susil | |
| 2003/0208252 A1 | 11/2003 | O'Boyle et al. | |
| 2003/0212373 A1 | 11/2003 | Hall et al. | |
| 2004/0015079 A1 | 1/2004 | Berger et al. | |
| 2004/0034338 A1 | 2/2004 | Thierfelder et al. | |
| 2005/0070972 A1 | 3/2005 | Wahlstrand et al. | |
| 2005/0222658 A1 | 10/2005 | Hoegh et al. | |
| 2006/0009819 A1 | 1/2006 | Przybyszewski | |

(56) References Cited

U.S. PATENT DOCUMENTS

| | | | |
|---|---|---|---|
| 2006/0100506 | A1 | 5/2006 | Halperin |
| 2006/0211979 | A1 | 9/2006 | Smith et al. |
| 2006/0247684 | A1 | 11/2006 | Halperin |
| 2007/0112398 | A1 | 5/2007 | Stevenson |
| 2007/0167867 | A1 | 7/2007 | Wolf |
| 2007/0168005 | A1 | 7/2007 | Gray |
| 2007/0288058 | A1 | 12/2007 | Halperin et al. |
| 2008/0049376 | A1 | 2/2008 | Stevenson |
| 2008/0071313 | A1 | 3/2008 | Stevenson |
| 2008/0116997 | A1 | 5/2008 | Dabney |
| 2008/0132987 | A1 | 6/2008 | Westlund |
| 2008/0161886 | A1 | 7/2008 | Stevenson et al. |
| 2008/0262592 | A1 | 10/2008 | Jordan et al. |
| 2008/0294162 | A1* | 11/2008 | Rossetto et al. ............... 606/50 |
| 2010/0023000 | A1 | 1/2010 | Stevenson et al. |
| 2011/0082359 | A1* | 4/2011 | Rey ............................ 600/393 |

FOREIGN PATENT DOCUMENTS

| | | |
|---|---|---|
| EP | 0 673 621 A1 | 9/1995 |
| JP | 6-70902 | 3/1994 |
| JP | 994238 | 4/1997 |
| WO | WO 87/04080 A2 | 7/1987 |
| WO | WO 92/10213 A1 | 6/1992 |
| WO | WO 94/23782 A1 | 10/1994 |
| WO | WO 97/40396 A1 | 10/1997 |
| WO | WO 98/52461 A1 | 11/1998 |
| WO | WO 00/10456 A1 | 3/2000 |
| WO | WO 00/25672 A1 | 5/2000 |
| WO | WO 02/083016 A1 | 10/2002 |

OTHER PUBLICATIONS

C. Gabriel, S. Gabriel and E. Corthout, "I. Dielectric Properties of Biological Tissues: Literature Survey," 1996, IOP Publishing Ltd.

S. Gabriel, R.W. Lau and C. Gabriel, "II. Dielectric Properties of Biological Tissues: Measurements and the Freuency Range 0 Hz to 20 GHz,"Phys. Med. Biol. 41, 1996, pp. 2251-2269, IOP Publishing Ltd.

S. Gabriel, R.W. Lau and C. Gabriel, "III. The Dielectric Properties of Biological Tissues: Parametric Models for the Dielectric Spectrum of Tissues," Phys. Med. Biol. 41, 1996, pp. 2271-2293, IOP Publishing Ltd.

Constantine A. Balinis, "Advanced Engineering Electromagnetics," 1989, John Wiley & Sons.

Robert C. Susil, Henry R. Halperin, Christopher J. Yeung, Albert C. Lardo and Ergin Atalar, "Multifunctional Interventional Devices for MRI: A Combined Electrophysiology/MRI Catheter," Magnetic Resonance in Medicine, 47: 594-600, 2002.

Mauritis K. Konings, Lambertus W. Bartels, Henk F.M. Smits and Chris J.G. Bakker, "Heating Around Intravascular Guidewires by Resonating RF Waves," Journal of Magnetic Resonance Imaging, 12:79-85, 2000.

Michael J. Weiner, Wilson Greatbatch, Patrick R. Connelly, U.S. Appl. No. 60/269,817, filed Feb. 20, 2001, entitled "Electromagnetic Interference Immune Cardiac Assist System."

Bruce L. Wilkoff M.D., "ICD Extraction Infected/Redundant Leads—Everyday Clinical Practice," Cleveland Clinic, ICD Lead Extraction, Every Day Practice.

* cited by examiner

PATIENT ATTACHED BONDING STRAP FOR ENERGY DISSIPATION FROM A PROBE OR A CATHETER DURING MAGNETIC RESONANCE IMAGING

CROSS-REFERENCE TO RELATED APPLICATIONS

None.

DESCRIPTION

1. Field of the Invention

The present invention generally relates to medical probes and catheters. More particularly, the present invention relates to a conductive mesh attached to a patient during magnetic resonance imaging for dissipation of imparted energy along a probe or catheter to an energy dissipating surface.

2. Background of the Invention

Catheter ablation has become an increasingly popular procedure to stop atrial fibrillation or ventricular arrhythmias. Typically, in the prior art, CT imaging and real-time fluoroscopy overlay is used to ablate precise landmarks. For example, in atrial fibrillation, ablation typically would be performed by inserting a catheter into the femoral artery and then routing it transvenously into the atrium. This is a highly skilled procedure in that, to successfully ablate the proper area, particularly in patients with intermittent atrial fibrillation, one must create a continuous ring of scar tissue around the pulmonary vein where they enter the atrium to isolate the pulmonary veins from the rest of the heart. This continuous ring of scar tissue is critical as isolation of the pulmonary veins from the rest of the heart prevents any pulses from these veins from getting into the heart, thus triggering atrial fibrillation. Creating a perfect circular scar as it is being formed, however, is very difficult because one cannot visualize the scar tissue in the prior art imaging techniques.

Catheter ablation is also a very common procedure for ablating lesions or cancer tumors. For example, it is used in stereotactic techniques to ablate brain, liver, lung, and non-palpable breast lesions or tumors. The entrance for this can be through the front (through the pectoral muscle) or through the back. Similarly, many other cancer tumors can be ablated in this manner. Correspondingly, catheter ablation can be performed transvenously or by tunneling through body tissues. The present invention is applicable to both cases.

Accordingly, there is a need for a method of performing catheter or probe RF ablation while in the presence of a magnetic resonance imaging (MRI) system. The ability to visualize scar formation is unique to MRI. An MRI enabled catheter wherein the physician could see clearly the MRI images of the inside of the atrium along with where scars are formed would be a very important improvement in patient outcomes.

While an MRI enabled catheter offers the opportunity to effectively visualize ablated (scar) tissue, it has been well demonstrated that any elongate leadwire placed on or inside the human body during MRI can pick up energy from the MRI RF-pulsed field. This energy can be deposited on the lead in such a way that its distal electrode(s) overheat. It would be highly undesirable for the RF ablation tip electrode or sensing electrodes to overheat during routing or ablation inside the ventricle. The reason for this is inadvertent ablation may occur in the wrong place. For example, if the sinus node is ablated, the patient would become pacemaker dependent for the rest of their lives. Hence, the ability to use MRI for real-time ablation is dependent on the development of probes and catheters that have filtering and design techniques such that they will not inappropriately or inadvertently overheat during the MRI procedure.

The present invention is directed towards energy dissipation frequency selective components located in the handle of a probe or catheter. In addition, the present invention is directed towards methods for providing an RF bonding cable (strap) from the probe or catheter handle or pistol grip to a skin surface location. Maximal energy can then be drawn from the conductors of the probe or catheter and redirected away from distal electrodes towards a proximal energy dissipating surface, which includes skin surfaces.

SUMMARY OF THE INVENTION

An exemplary embodiment of the present invention includes a probe or catheter to patient RF coupling for magnetic resonance imaging. A conductive grounding strap includes a first end spaced apart from a second end. The first end is configured to be permanently or removably connectable to a conductive probe or catheter housing or a conductive probe or catheter interface of a probe or catheter. A conductive patient interface is configured to be removably connectable to a portion of a patient's body and electrically conductive between the conductive grounding strap and the patient's body. The conductive patient interface is attached at the second end of the conductive grounding strap and electrically coupled to the conductive probe or catheter housing or the conductive probe or catheter interface.

In other embodiments, the conductive grounding strap may include a solid metal foil strap, a braided metal strap, or a metal mesh strap. The conductive grounding strap may include a protective or insulative covering. The metal may include copper, nickel, silver, carbon, titanium, stainless steel, chromium cobalt, nitinol, tantalum, tungsten, iridium, or platinum. The metal may include a plating, the plating including tin, gold, silver, or nickel. The conductive grounding strap may include a flexible conductive grounding strap. The conductive grounding strap may include a substantially flat conductive grounding strap. The conductive grounding strap may be at least one-half of an inch wide. Alternatively, the conductive grounding strap may be at least one inch wide.

The conductive patient interface may include a wrist strap, forearm strap, arm strap, ankle strap, calf strap, thigh strap, foot sock, hand sock, head band, head cap, glove, sock, patch, table, pad, vest or gown.

An insulative handle of the probe or catheter may include a proximal and distal end wherein the conductive probe or catheter housing or conductive probe or catheter interface is disposed inside the probe or catheter handle.

At least one probe or catheter body conductor may be disposed inside the probe or catheter handle between the proximal and distal ends of the probe or catheter handle. A frequency selective diverter circuit may be electrically coupled between the at least one probe or catheter body conductor and the conductive probe or catheter housing or conductive probe or catheter interface. A frequency selective impeder circuit may be disposed in series along the at least one probe or catheter body conductor between the frequency selective diverter circuit and the proximal end of the probe or catheter handle. A second frequency selective diverter circuit may be electrically coupled between the at least one probe or catheter body conductor and the conductive probe or catheter housing or conductive probe or catheter interface, wherein the second frequency selective diverter circuit is disposed between the frequency selective impeder circuit and the proximal end of the probe or catheter handle. The frequency selective diverter circuit may include a capacitor or an LC trap filter. The frequency selective impeder circuit may include a bandstop filter or an inductor. The second frequency selective diverter circuit may include a capacitor or an LC trap filter.

A conductive connector may be disposed in series along the conductive grounding strap between the first and second ends, wherein the conductive connector is removably connectable separating and connecting the first and second ends.

An electrical circuit may be formed between the patient's body, the conductive patient interface, the conductive grounding strap, and the conductive probe or catheter housing or interface.

Another exemplary embodiment of the present invention includes a probe or catheter including a probe or catheter handle having a proximal and distal end. A conductive probe or catheter housing or a conductive probe or catheter interface is disposed inside the probe or catheter handle. At least one probe or catheter body conductor is disposed inside the probe or catheter handle between the proximal and distal ends of the probe or catheter handle and electrically coupled to the conductive probe or catheter housing or conductive probe or catheter interface. A frequency selective diverter circuit is electrically coupled between the at least one probe or catheter body conductor and the conductive probe or catheter housing or conductive probe or catheter interface. A conductive grounding strap includes a first end spaced apart from a second end, the first end configured to be permanently or removably connectable to the conductive probe or catheter housing or conductive probe or catheter interface. A conductive patient interface is configured to be removably connectable to a portion of a patient's body and electrically conductive between the conductive grounding strap and the patient's body. The conductive patient interface is disposed at the second end of the conductive grounding strap and electrically coupled to the conductive probe or catheter housing or conductive probe or catheter interface.

In other embodiments, a frequency selective impeder circuit may be disposed in series along the at least one probe or catheter body conductor between the frequency selective diverter circuit and the proximal end of the probe or catheter handle. A second frequency selective diverter circuit may be electrically coupled between the at least one probe or catheter body conductor and the conductive probe or catheter housing or conductive probe or catheter interface, wherein the second frequency selective diverter circuit may be disposed between the frequency selective impeder circuit and the proximal end of the probe or catheter handle. The frequency selective diverter circuit may include a capacitor or an LC trap filter. The frequency selective impeder circuit may include a bandstop filter or an inductor. The second frequency selective diverter circuit may include a capacitor or an LC trap filter.

The conductive patient interface may include a wrist strap, forearm strap, arm strap, ankle strap, calf strap, thigh strap, foot sock, hand sock, head band, head cap, glove, sock, patch, table, pad, vest or gown.

A probe or catheter body extension may include a near end and a far end, the near end removably or permanently connectable to the distal end of the probe or catheter handle. The far end of the probe or catheter body extension may include an ablation tip electrode. The far end of the probe or catheter body extension may include a first ring electrode and a second ring electrode. The ablation tip electrode may be electrically coupled to the at least one probe or catheter body conductor.

A frequency selective ablation tip impeder circuit may be disposed at, near or within the ablation tip electrode. The frequency selective ablation tip impeder circuit may include a bandstop filter or an inductor. The far end of the probe or catheter body extension may include a mapping electrode.

An electrical circuit may be formed between the patient's body, the conductive patient interface, the conductive grounding strap, the conductive probe or catheter housing or interface, and the at least one probe or catheter body conductor.

Another exemplary embodiment of the present invention includes a probe or catheter to patient RF coupling for magnetic resonance imaging. A conductive grounding strap includes a first end spaced apart from a second end, the first end configured to be permanently or removably connectable to a conductive probe or catheter interface of a probe or catheter body extension. A conductive patient interface is configured to be removably connectable to a portion of a patient's body and electrically conductive between the conductive grounding strap and the patient's body, the conductive patient interface attached at the second end of the conductive grounding strap and electrically coupled to the conductive probe or catheter interface.

In other embodiments, at least one conductor may be disposed inside the probe or catheter body extension. A frequency selective diverter circuit may be electrically coupled between the at least one conductor and the conductive probe or catheter interface. A frequency selective impeder circuit may be disposed in series along the at least one conductor between the frequency selective diverter circuit and a proximal end of the probe or catheter body extension. A second frequency selective diverter circuit may be electrically coupled between the at least one conductor and the conductive probe or catheter interface, wherein the second frequency selective diverter circuit may be disposed between the frequency selective impeder circuit and the proximal end of the probe or catheter body extension. The frequency selective diverter circuit may include a capacitor or an LC trap filter. The frequency selective impeder circuit may include a bandstop filter or an inductor. The second frequency selective diverter circuit may include a capacitor or an LC trap filter. A conductive connector may be disposed in series along the conductive grounding strap between the first and second ends, wherein the conductive connector is removably connectable separating and connecting the first and second ends. An electrical circuit may be formed between the patient's body, the conductive patient interface, the conductive grounding strap, the conductive probe or catheter interface, and the probe or catheter body extension.

Other features and advantages of the present invention will become apparent from the following more detailed description, when taken in conjunction with the accompanying drawings, which illustrate, by way of example, the principles of the invention.

DETAILED DESCRIPTION OF THE PREFERRED EMBODIMENTS

Figure 1:
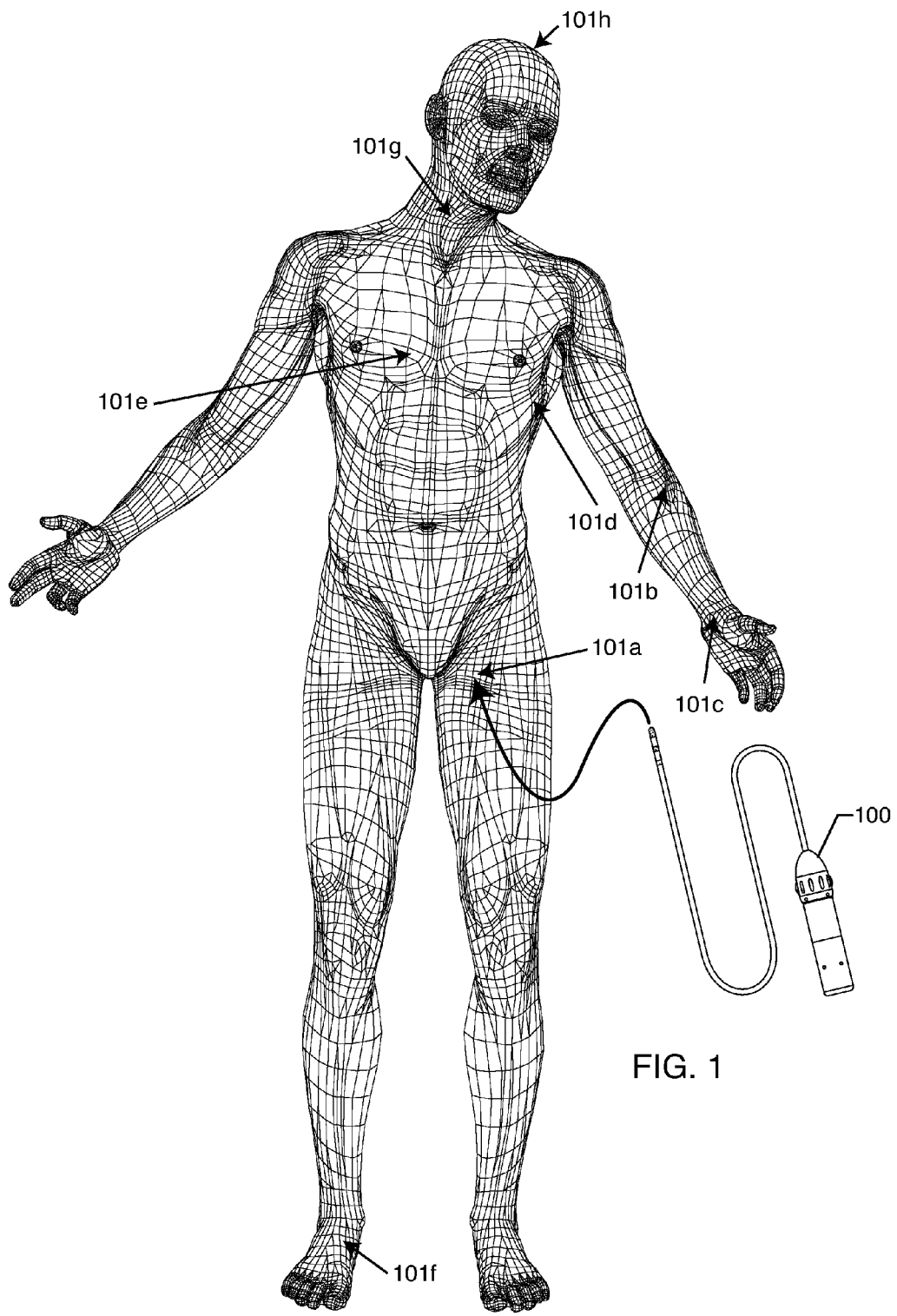
FIG. 1 illustrates a wire-formed diagram of a generic human body showing a probe or catheter inserted into the femoral artery.

FIG. 1 illustrates a prior art wire form diagram of a generic human body showing a typical probe or catheter 100 inserted into the femoral artery at approximately location 101a. Alternative locations for either transvenous, percutaneous or laparoscopic insertion are shown in locations 101b, 101c (wrist venous access), 101d, which would be transthoracic for ablation outside of cardiac chambers, 101e, which would be a tunneling to perhaps ablate a lung tumor, 101f, which would gain venous access in the ankle, 101g to access the Carotid or other arteries of the neck, or 101h, an entrance to access through the top of the valve, which would at that time be open.

Figure 2:
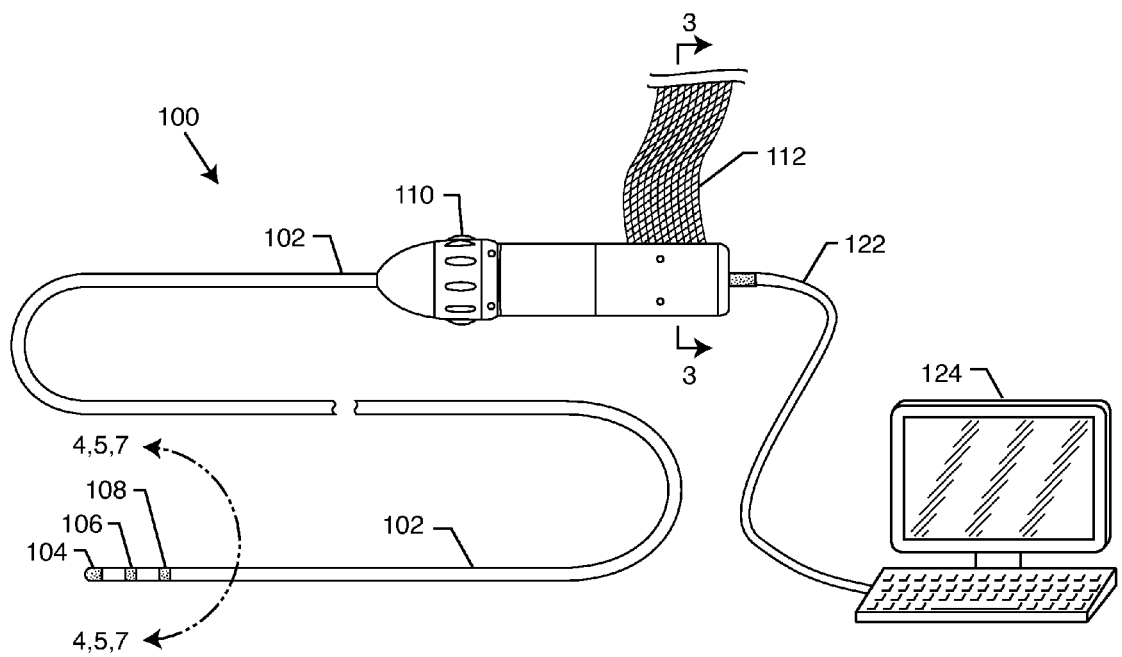
FIG. 2 illustrates an exemplary probe or catheter embodying the present invention.

FIG. 2 illustrates an exemplary probe or catheter 100 embodying the present invention. As used herein, the words "probe" and "catheter" are interchangeably used throughout. All embodiments of the present invention can be applied to the wide range of probe or catheter designs. A catheter body extension 102 extends from the probe/catheter 100. A distal electrode 104, which in this case would be an ablation tip electrode 104, is located at the far end of the catheter body extension 102. There are also sensing electrodes 106 and 108 for mapping of electrical signals in or alongside the heart. The steerable catheter handle 110 is shown. This is used to be able to guide the catheter through the torturous path through tissue tunneling or through the venous system. A novel RF bond strap 112 is shown. This novel bond strap 112 is designed to be directly attached or connected to patient tissue (not shown) and/or a thermally conductive pad or mat in contact with patient tissue. The probe or catheter handle 110 is also connected with a cable 122 to either RF ablation generating equipment or cardiac electrical mapping programmer 124.

Figure 3:
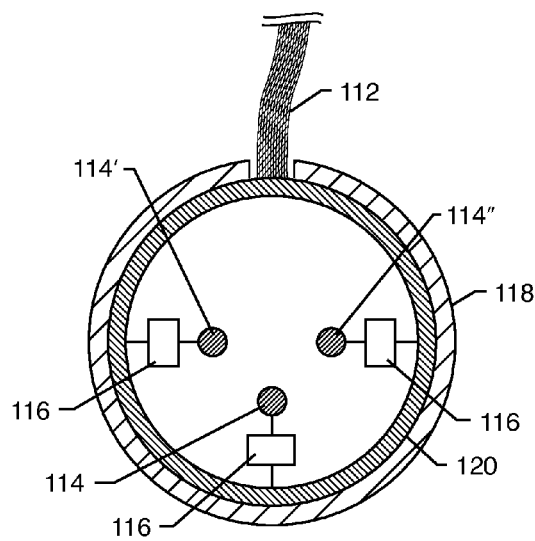
FIG. 3 illustrates a sectional view of the structure of FIG. 2 taken along lines 3-3.

FIG. 3 is a sectional view of the structure of FIG. 2 taken along line 3-3 showing the interior of the handle 110 as well as the cross-section of the RF bonding strap 112. The purpose of the bonding strap 112 is to divert MRI RF-pulsed energy out of the probe 100 or handle 110 to a patient surface where it can be dissipated over a large surface area where a minimal temperature rise would occur adjacent the patient. The RF bonding strap 112 provides a low impedance at MRI RF-pulsed frequencies, such as 64 MHz or 128 MHz. It is important that the RF bonding strap 112 has a form factor that is relatively wide and is also relatively thick as shown in FIGS. 2 and 3. It is very important that the RF bonding strap 112 has both a low resistance and a low inductance. The resistance is a property of the material, its cross-sectional area and its length. Accordingly, in a preferred embodiment, the RF bonding strap would be of copper or other highly conductive metal. It is also important that the RF strap 112 be kept relatively short.

Referring once again to FIG. 3, one can see that there are three catheter body conductors 114, 114', 114" which are routed to the three electrodes 104, 106 and 108. Inside of the probe or catheter handle 110 or pistol grip 110 are frequency selective diverter elements 116. As previously described in patent application Ser. No. 12/686,137 filed Jan. 12, 2010, and also patent application Ser. No. 12/751,711 filed on Mar. 31, 2010, (the contents of which are fully incorporated herein by this reference) these diverter elements 116 can consist of either a capacitor 140 or an L-C trap filter 148. In both cases, the diverter element 116 is designed to present a very low impedance path between the catheter body conductors 114 and the conductive housing/interface 120 located within the catheter probe or handle cover 118. This diverts high frequency energy from the catheter body conductors 114 to the probe or catheter conductive surface 120. Conductive surface 120 may be electrically or thermally conductive, or a combination of both. The optional insulation 118 is shown which can be placed over the probe or catheter handle 110.

It is important that the grounding strap 112 have a direct electrical connection to the metal surface 120. The diverter elements 116 work best when there are distal bandstop filters 146 placed at, near or within electrodes 104, 106, 108. It will be obvious to those skilled in the art that any number of electrodes or electrode configurations could be used. Three are shown for simplicity in the present invention. Bandstop filters 146 are well known in the prior art and are previously described in U.S. Pat. Nos. 7,363,090; 8,116,862; 8,145,324; and 8,155,760, the contents of which are fully incorporated herein with this reference. When there is a bandstop filter 146 at, near or within the distal electrodes 104, 106 or 108, a high impedance at the distal electrode end is created which tends to make the distal end appear open or unconnected. When this occurs it creates a reflection causing energy to be sent back in the other direction. In the case of MR guided catheter ablation, electro-motive forces (EMFs), or E·dl, are introduced all along the length of the ablation catheter, that is, along the length of the conductor. As a result, that parcel of energy being transmitted along the length of the conductor, namely the MRI RF energy, reflects off the distal tip band stop filter 146 back towards the catheter handle 110 and then back again toward the distal tip. This creates a worse case heating situation at the distal end unless the heat can be redirected to be safely dissipated via an energy dissipating surface. Accordingly, it is important to capture this energy and divert it to a high surface area energy dissipating surface which can be a portion of the patient's body or another thermally conductive medium such as a pad or a mat. The importance of providing an energy dissipating surface at the proximal end of catheter body extension 102 is dramatically illustrated in FIG. 2 of a paper entitled, PACEMAKER LEAD TIP HEATING IN ABANDONED AND PACEMAKER-ATTACHED LEAD AT 1.5 TESLA MRI. This paper was printed in the Journal of Magnetic Resonance Imaging, 33:426-431 (2011). The paper was written by researchers at UCLA and dramatically illustrates how an energy dissipating surface, in this case, a cardiac pacemaker, can pull energy from the lead and dissipate it into surrounding tissues. This paper is fully incorporated herein by this reference.

Figure 4:
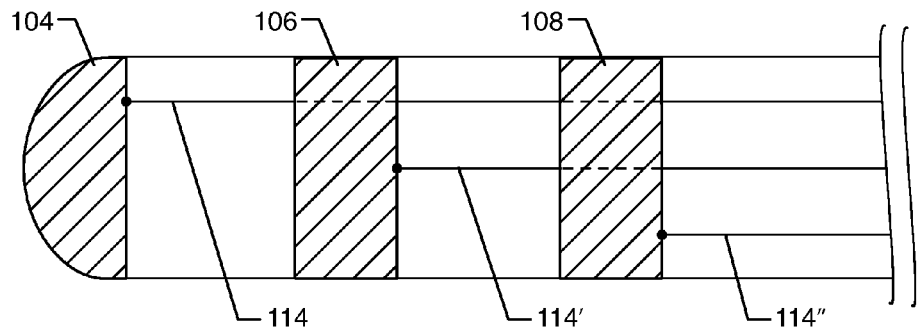
FIG. 4 illustrates an embodiment of an enlarged sectional view of the structure of FIG. 2 taken along lines 4-4.

FIG. 4 is an embodiment of an enlarged sectional view of the structure of FIG. 2 taken along lines 4-4 and illustrates a close-up of the distal ablation electrode 104 and the two sensing electrodes 106 and 108. Shown are internal catheter or probe body conductors 114, 114' and 114".

Figure 5:
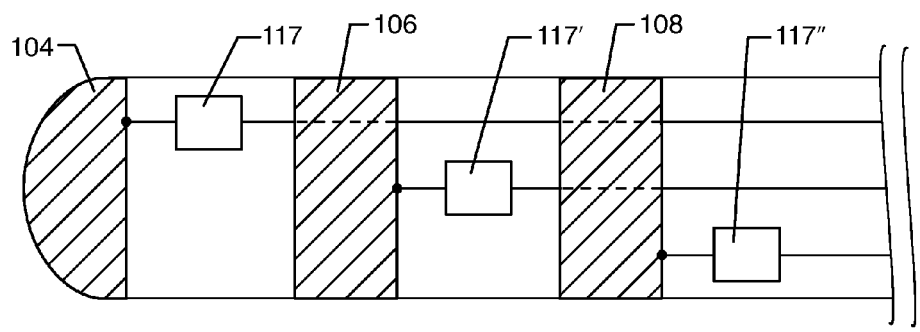
FIG. 5 illustrates another embodiment of an enlarged sectional view of the structure of FIG. 2 taken along lines 5-5.

FIG. 5 is another embodiment of an enlarged sectional view of the structure of FIG. 2 taken along lines 5-5 and is very similar to FIG. 4 except that it now shows frequency variable impeder elements 117, 117' and 117".

Figure 6:
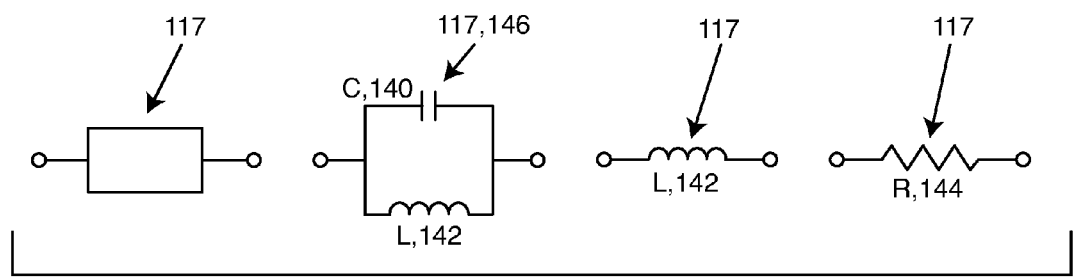
FIG. 6 illustrates a multitude of impeder elements.

FIG. 6 illustrates the impeder elements 117 as previously described in FIG. 5. The impeder element 117 may include a bandstop filter 146 comprised of a capacitor 140 in parallel with an inductor 142. The center resonant frequency of the bandstop filter 146 would be selected by the values of inductance and capacitance. The 3-dB bandwidth and Q of the bandstop filter 146 is determined by the resistor elements of the inductor 142 and the capacitor 140 (not shown). A thorough description of Q and 3-dB bandwidth is provided in U.S. Pat. Nos. 7,363,090; 8,116,862; 8,145,324; and 8,155,760 which are fully incorporated herein by this reference. The impeder elements can also include either an inductor 142 or a resistor 144.

The impeder element 117 may include an inductor 142. The impeder element 117 may also include a resistor 144. The impeder element 117 could also be any of the elements shown in FIG. 6 acting together. For example, one could have a bandstop filter 146 consisting of the inductor parallel to the capacitance at, near or within the distal tip electrode 104 and also have distributed inductance L and distributed resistance R along the rest of the catheter body conductor 114.

Figure 7:
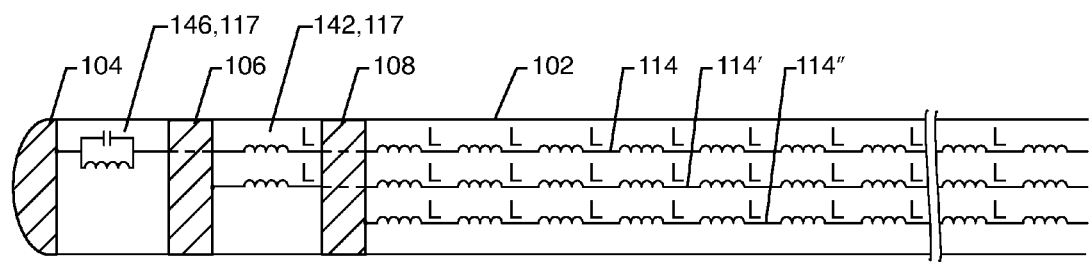
FIG. 7 illustrates another embodiment of an enlarged sectional view of the structure of FIG. 2 taken along lines 7-7.

FIG. 7 illustrates a bandstop filter 146 adjacent the distal electrode 104 and then discrete inductors L-142 shown along all or a portion of the conductors 114. It is not always necessary that a bandstop filter 146 be associated with a distal electrode. For example, in the case of biological sensing electrodes 106 and 108, inductance (or resistance) may be all that is required. In this case, a higher value of resistance is accessible because very little current is flowing in this biological sensing circuit. This is not the case for the ablation tip electrode 104 which must conduct a substantial amount of current to properly ablate human tissues. Accordingly, the resistance of this circuit must be relatively low.

Figure 8:
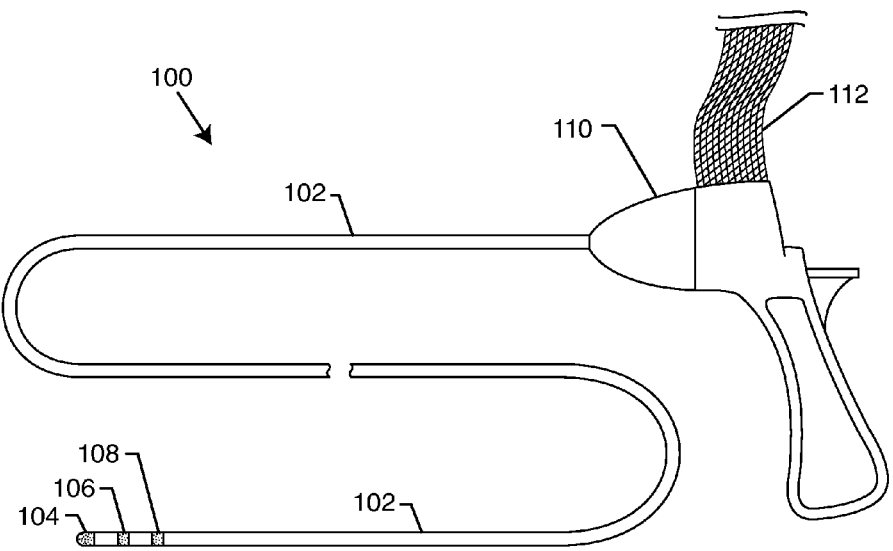
FIG. 8 illustrates another exemplary probe or catheter embodying the present invention.

FIG. 8 is very similar to FIG. 2 except in this case, the probe or catheter handle 110 has the form of a pistol grip. An RF ground strap or bonding strap 112 is illustrated. As described for FIGS. 2 and 3, it is important that this bonding strap 112 be attached directly to the conductive housing or interface 120 of the pistol grip.

Figure 9:
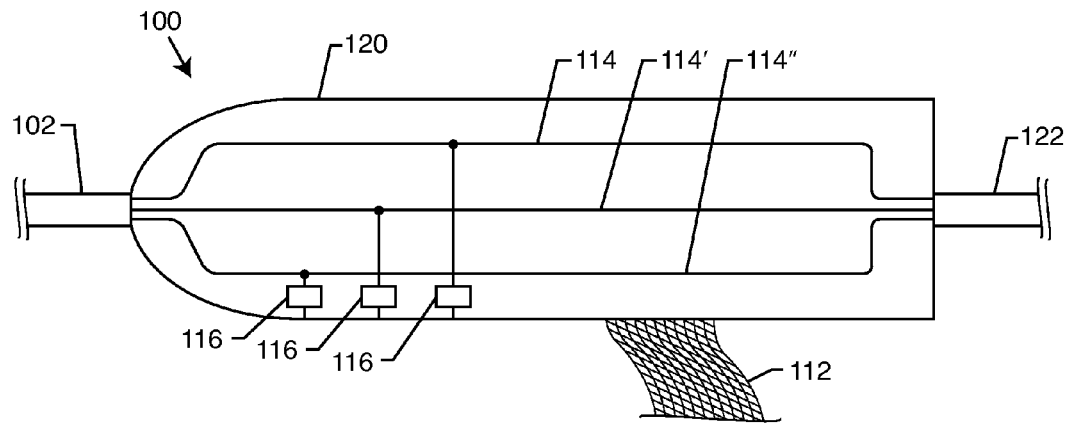
FIG. 9 illustrates a representative electrical schematic of the structure of FIG. 2.

FIG. 9 is a modified electrical schematic of the structure of FIG. 2 showing that diverter elements 116 are placed inside the catheter handle 110. As previously noted, this handle can take many forms, including cylindrical, pistol grip and the like. Referring once again to FIG. 9, handle 110 includes an electrically conductive metallic surface/housing/interface 120. The diverter elements 116 are connected between each of the conductors 114 and the metallic housing 120 which acts as an overall ground. One can also see the RF bond/ground strap 112 is also electrically connected to the electrical conductive surface 120. As previously mentioned, the diverter elements 116 can be capacitors 140, L-C traps 148, or even a wide family of low pass filters.

Figure 10:
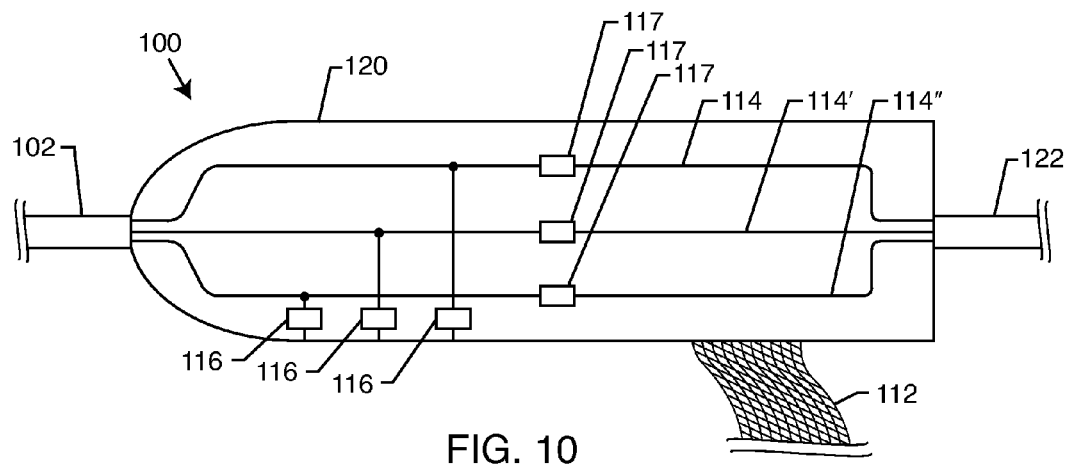
FIG. 10 illustrates another representative electrical schematic of the structure of FIG. 2.

FIG. 10 is very similar to FIG. 9 showing that impeders 117 can be used in combination with diverters 116. In this embodiment, the impeders 117 could be bandstop filters 146, inductors 142 or the like.

Figure 11:
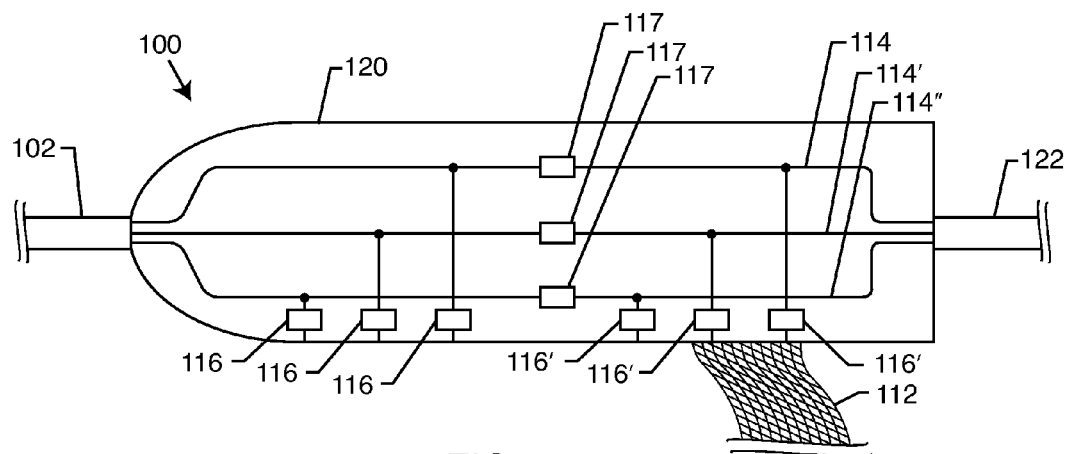
FIG. 11 illustrates another representative electrical schematic of the structure of FIG. 2.

FIG. 11 is very similar to FIGS. 9 and 10 illustrating that any number of diverters 116 and impeders 117 can be used. For example, in FIG. 11, diverters 116 could be capacitors 140 and impeders 117 could be bandstop filters 146 and diverters 116' could be L-C trap filters 148. This type of multi-element filter approach would not only draw a substantial amount of RF energy out of the conductors 114 of the probe or catheter, but this circuit would also provide a very high degree of EMI filter protection to electronic devices 124, such as those previously illustrated in FIG. 2. In other words, if there were sensitive biological sensing or electrical activity mapping equipment 124, it is important to keep the pulse field of the MRI equipment from interfering with said electronics.

Figure 12:
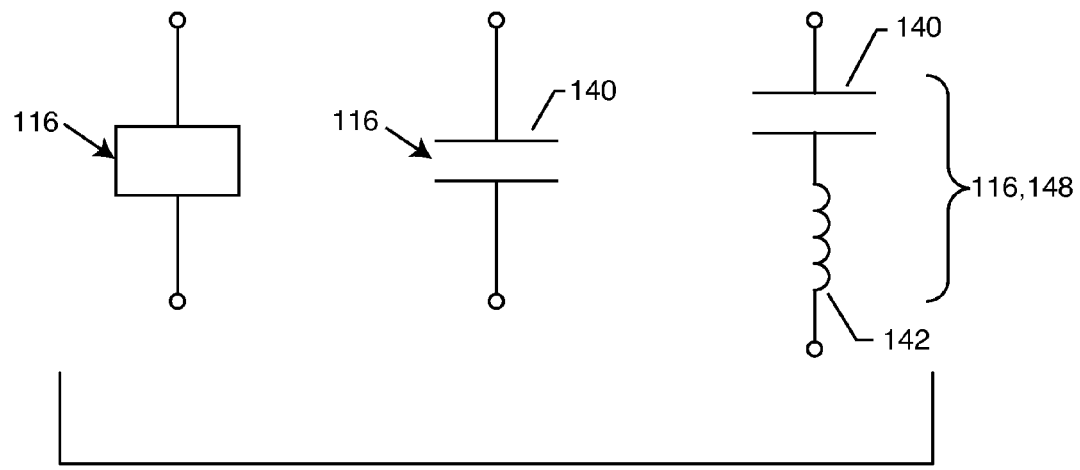
FIG. 12 illustrates a multitude of diverter elements.

FIG. 12 illustrates the various forms of diverter elements 116, including a general diverter 116, a capacitor inverter 140 and an L-C trap filter 148 consisting of capacitor 140 and inductor 142. For the L-C trap filter 148, the values of capacitance 140 and inductance 142 would be carefully selected such that the L-C trap filter 148 is resonant at the MRI RF-pulsed frequency. Those skilled in the art will realize that when an L-C trap filter 148 is at resonance, it presents a very low impedance (short circuit) at that frequency. For the L-C trap filter 148, the resistance from the inductor 142 and the equivalent series resistance of the capacitor 140 is not shown. Those skilled in the art will realize that one can control the 3-dB bandwidth or Q of the L-C trap filter 148 by controlling the amount of resistance in both the capacitor 140 and the inductor 142. In a preferred embodiment, the 3-dB bandwidth of the L-C trap filter 148 would be a minimum of 10 kHz. In a further preferred embodiment, the 3-dB bandwidth would be on the order of megahertz or at least 0.5 MHz.

Figure 13:
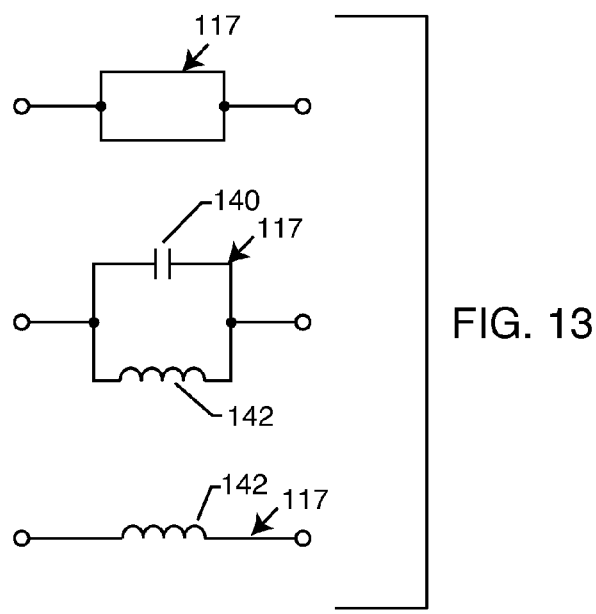
FIG. 13 illustrates a multitude of impeder elements.

FIG. 13 illustrates the impeder element 117 previously illustrated in FIGS. 10 and 11. The general impeder is shown as 117 when the impeder can consist of a capacitor 140 in parallel with inductor 142 thereby creating a parallel resonance L-C bandstop filter 146. Again, the value of capacitance 140 and inductance 142 would be carefully selected such that the bandstop filter 146 has a resonant center frequency at the MRI RF-pulsed frequency. Referring to U.S. Pat. Nos. 7,363,090; 8,116,862; 8,145,324; and 8,155,760, (which are fully incorporated herein by this reference) one can see how the Q and 3-dB bandwidth of the L-C bandstop filter 146 can be controlled by controlling the resistive elements of either the inductor 142 or the capacitor 140. In a preferred embodiment, the 3-dB bandwidth of the bandstop filter 146 would be at least 10 kHz. In other embodiments, the 3-dB bandwidth would be at least 0.5 MHz or even more than 10 MHz. In a cath lab with only one MRI scanner, the 3-dB bandwidth can be narrower. Typically, if only one area of the body is being imaged the gradient field does not significantly change the RF frequency. However, if one is looking at the broad spectrum of 1.5 Tesla MRI scanners, there is considerable variation in the static magnetic field strength from scanner to scanner. The Lamour Equation teaches that the RF-pulsed frequency is equal to 42.56 times the static magnetic field strength. Thus it is possible that the static magnetic frequency not only can vary sufficiently with a single manufacturer but also can vary significantly from manufacturer to manufacturer. As a result, there is a variation in RF frequency of over 0.5 MHz. FIG. 9 also illustrates that the diverter 116 can be a simple capacitor 140 whose impedance increases and becomes substantial at high frequencies such as MRI RF-pulsed frequencies.

Figure 14:
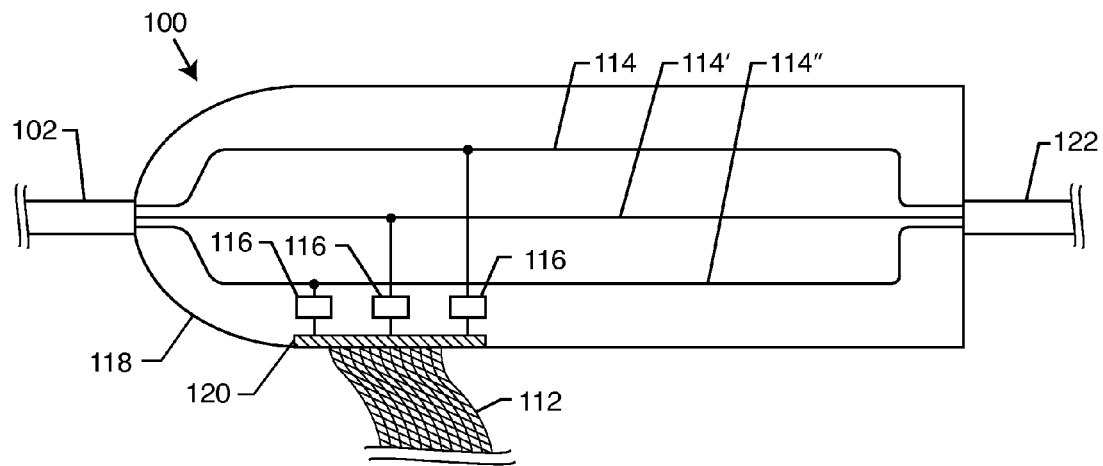
FIG. 14 illustrates a representative electrical schematic of the structure of FIG. 2, now showing a conductive interface.

FIG. 14 illustrates a representative electrical schematic of the structure of FIG. 2 now showing the conductive interface 120 as a smaller embodiment compared to FIGS. 9-11. The conductive interface 120 does not have to encompass the entirety of the inside of the catheter cover 118. The conductive interface 120 has to be large enough to allow a variety of electrical connections between the catheter body conductors 114 and the grounding strap 112.

Figure 15:
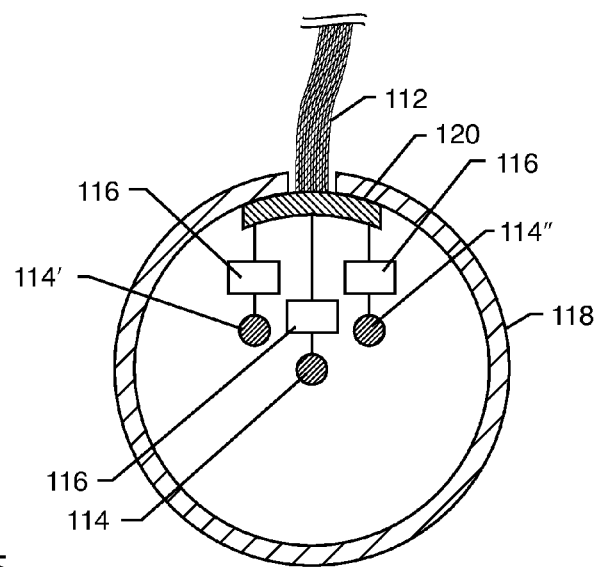
FIG. 15 illustrates a sectional view of the structure of FIG. 14 now showing the conductive interface.

FIG. 15 illustrates a sectional view of the structure of FIG. 14 now showing the conductive interface 120 connecting the catheter body conductors 114 to the grounding strap 112.

Figure 16:
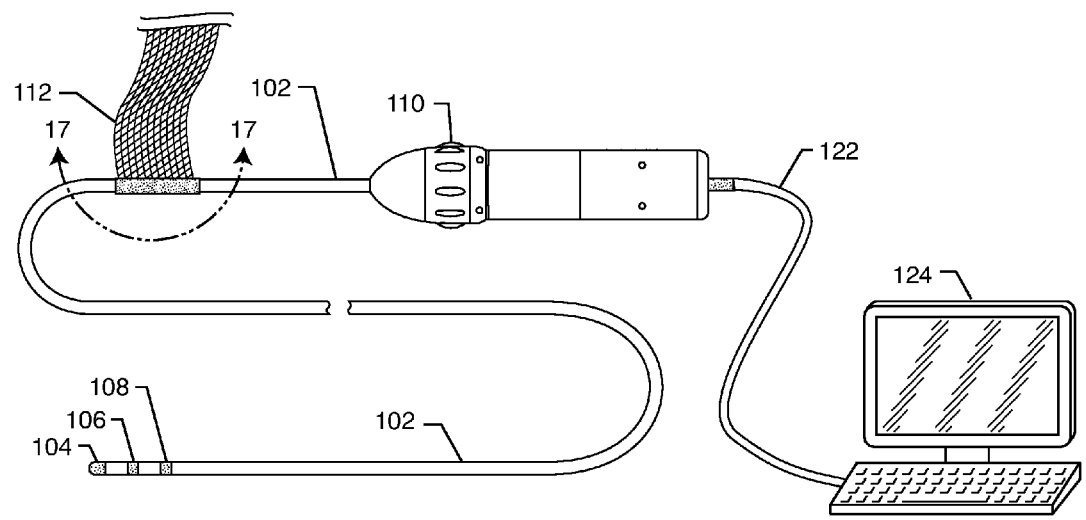
FIG. 16 illustrates an exemplary probe or catheter embodying the present invention, now with the strap connected to the body extension.

FIG. 16 illustrates an exemplary probe or catheter now with the grounding strap 112 connected to the body extension 102.

Figure 17:
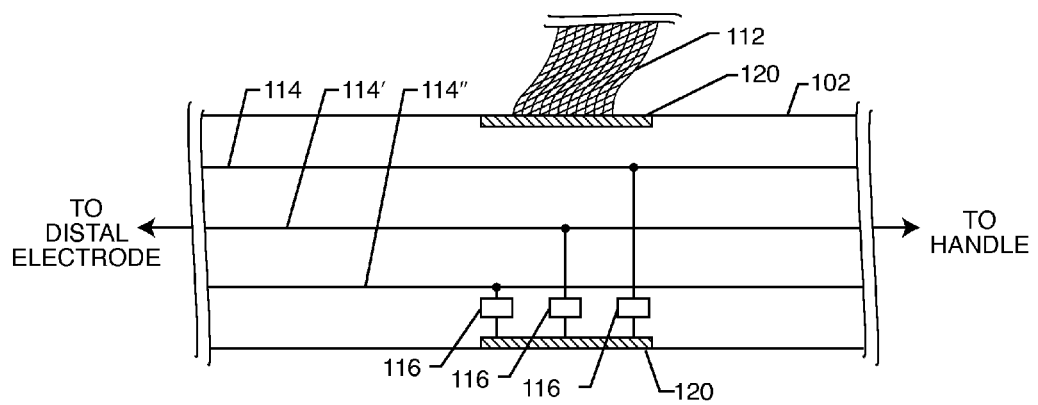
FIG. 17 illustrates an embodiment of an enlarged sectional view of the structure of FIG. 16 taken along lines 17-17.

FIG. 17 illustrates an embodiment of an enlarged sectional view of the structure of FIG. 16 taken along lines 17-17. The body extension 102 includes one or more conductors 114. These conductors 114 are electrically connected to various electrodes at the distal end of the body extension 102 and to the catheter handle 110. Frequency selective impeding and diverting circuits 116 and 117 can be located inside the body extension and arranged in similar configurations to FIGS. 9-11. Shown here are diverter elements 116 electrically connecting the conductors 114 to the conductive interface 120. The grounding strap 112 is then connected to the conductive interface 120.

Figure 18:
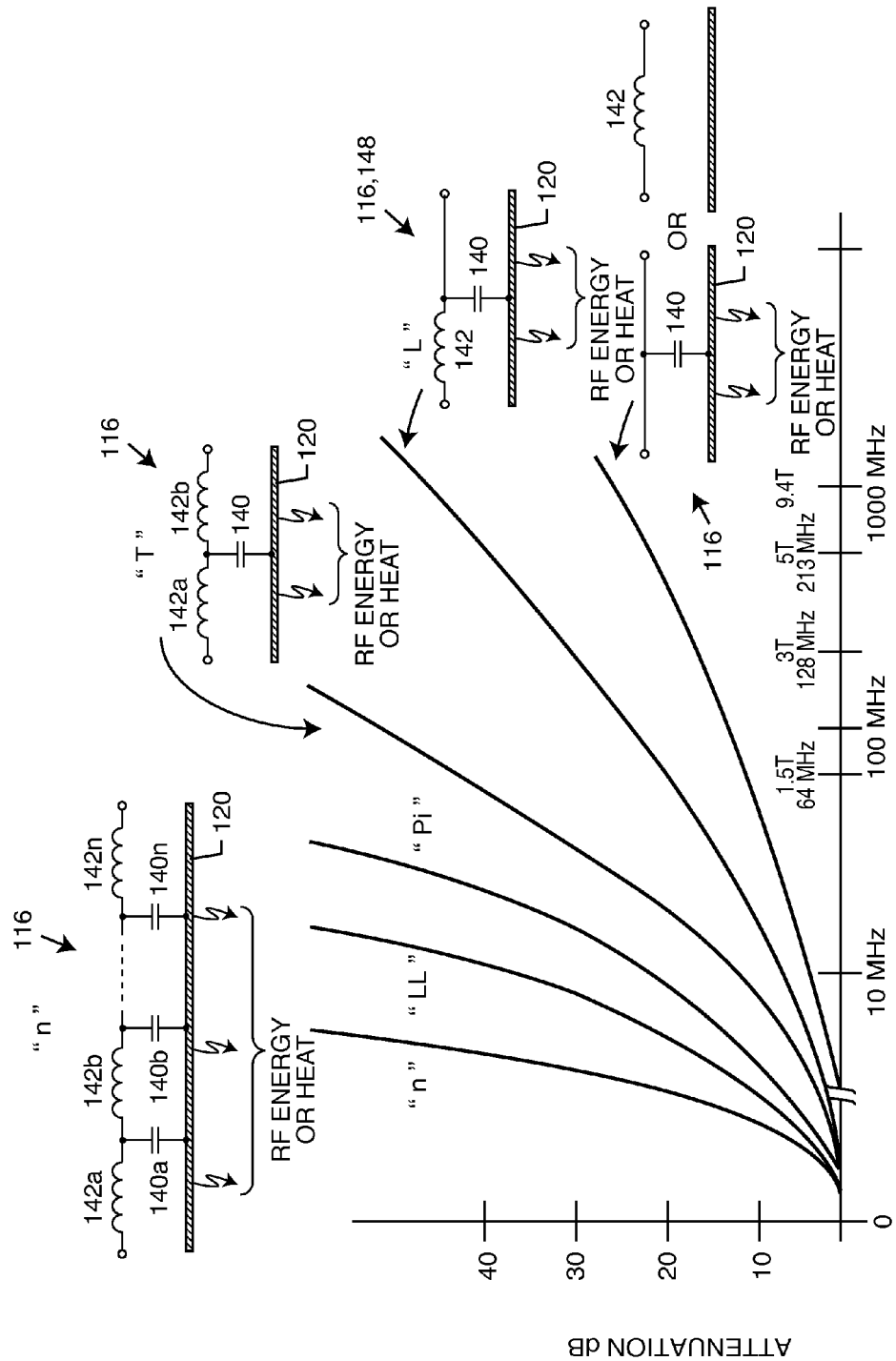
FIG. 18 illustrates a graph of attenuation versus frequency of various filter combinations.

FIG. 18 shows a family of low pass filter attenuation versus frequency curves. In the simplest embodiment, a low pass filter can be a single element capacitor 140 or a series inductor 142. One can see that the attenuation roll-off for a single element low pass filter is much lower than, for example, a two-element ("L") filter consisting of inductor 142 and capacitor 140. The "L" filter can have the inductor pointing to the left or the right (not shown). Also illustrated is a T-filter consisting of two inductors 142A and 142B with capacitor 140 directed to the ground or RF energy or heat dissipating surface 120. The Pi filter and LL filter combinations are well known to those skilled in the art, but are not shown to save space. The Pi filter is an analogue of the T-filter and has the same attenuation roll-off slope except that it has two capacitors separated by a single inductor. The "n" element indicates that any number of inductors and capacitors can be used in combination. It should also be pointed out that the "n" element filters can start with an inductor 142A or they can start with just the capacitor 140A (not shown).

Referring once again to FIG. 18, as described herein, the capacitor elements 140 can be considered to be RF energy diverters and the inductors 142 can be considered to be RF energy impeders. As one increases the number of diverters and impeders, one increases the efficiency or the attenuation of the filter. Accordingly, the filters that have the higher attenuation and dB will divert more RF energy from the lead conductor to the RF strap of the present invention.

Figure 19:
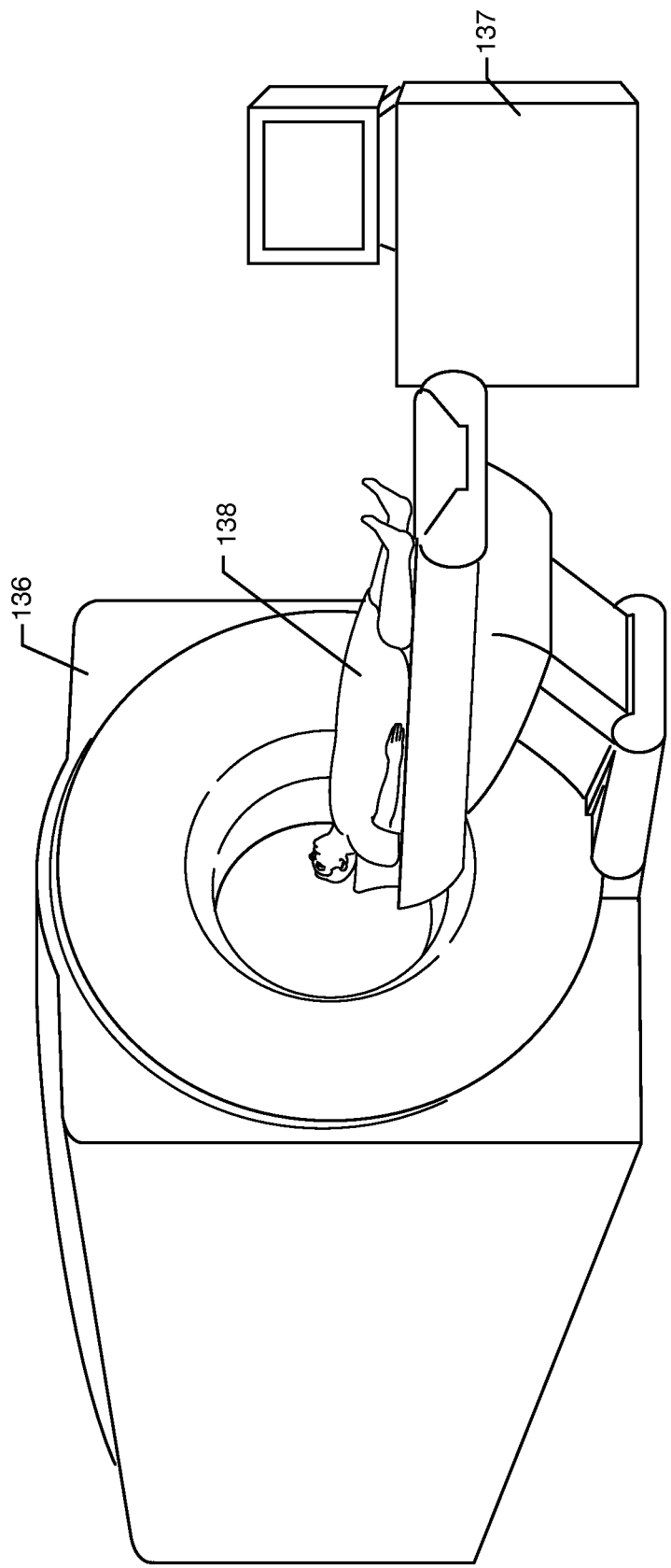
FIG. 19 illustrates a perspective view of a patient who is about to be placed into an MRI scanner.

FIG. 19 illustrates a prior art MRI scanner 136 with a patient 138 about to be positioned within the scanner. Also shown is MRI imaging processing equipment 137.

Figure 20:
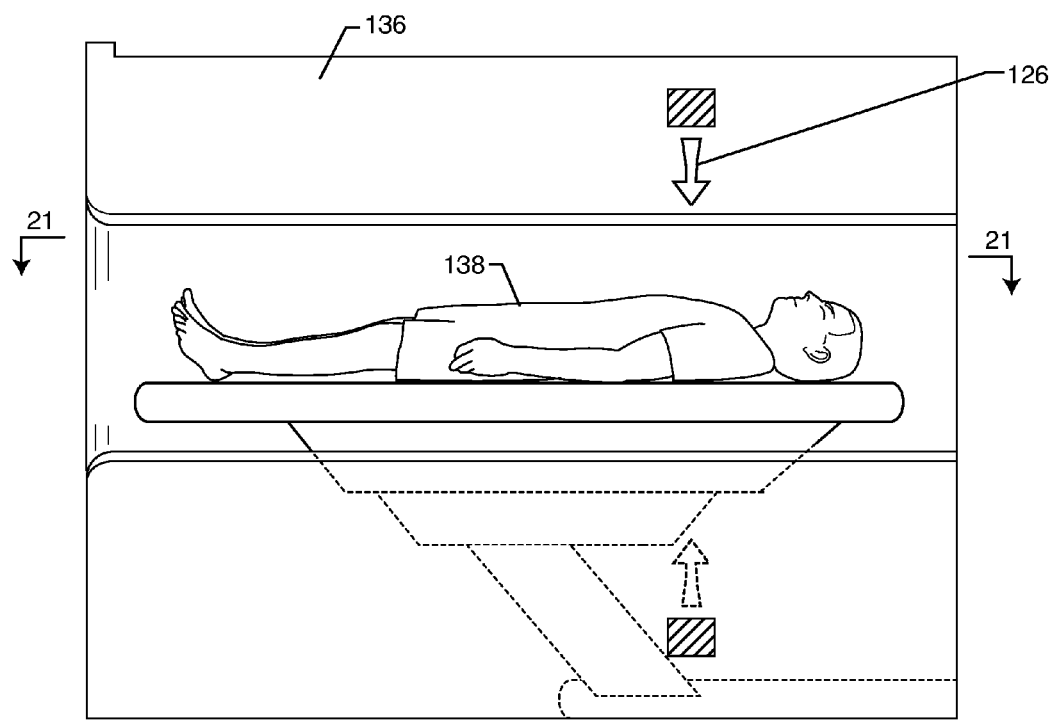
FIG. 20 illustrates a side view of the patient within the scanner showing an intense RF field impinging on the probe or catheter.

FIG. 20 illustrates a side view of the patient 138 placed inside of the scanner 136 and portrays that there is an intense RF field 126 to which the patient's entire body may be exposed. As previously mentioned, this intense MRI RF-pulsed field 126 can couple to implanted leadwires or to the conductors 114 of catheters and create substantial electromagnetic forces and currents. It is very important that the distal end of the catheter 102 and the electrodes 104, 106, 108 be protected from overheating in such an environment.

Figure 21:
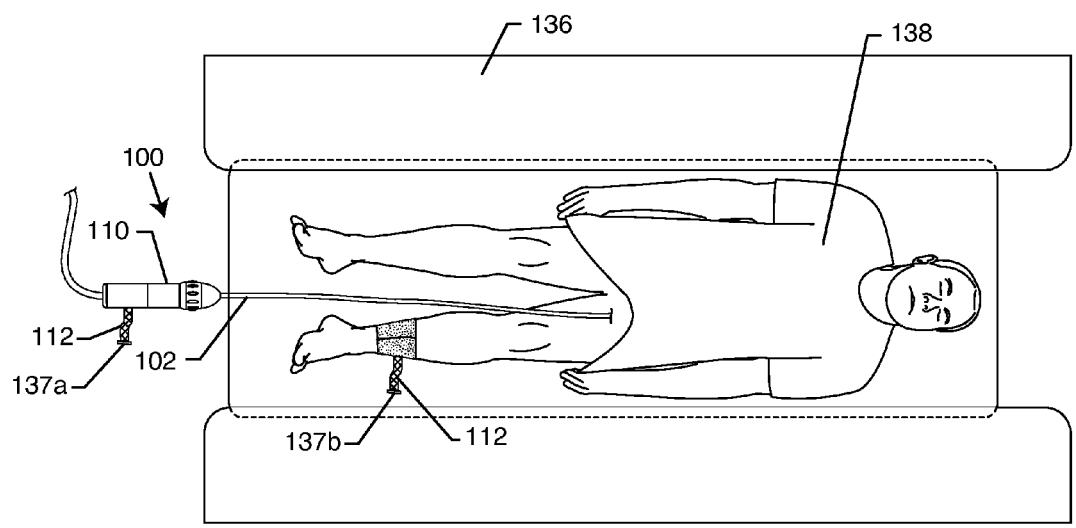
FIG. 21 illustrates a top view of the patient in the MRI scanner showing the insertion of a probe or catheter along the femoral artery.

FIG. 21 is a top view of the patient 138 inside the bore of the MRI scanner 136. One can see the catheter 100 consisting of the catheter handle 110 and the catheter body extension 102 inserted into the femoral artery of the patient's leg. As shown, the conductors 114 of the catheter body extension 102 would be exposed to the intense MRI RF field 126.

Figure 22:
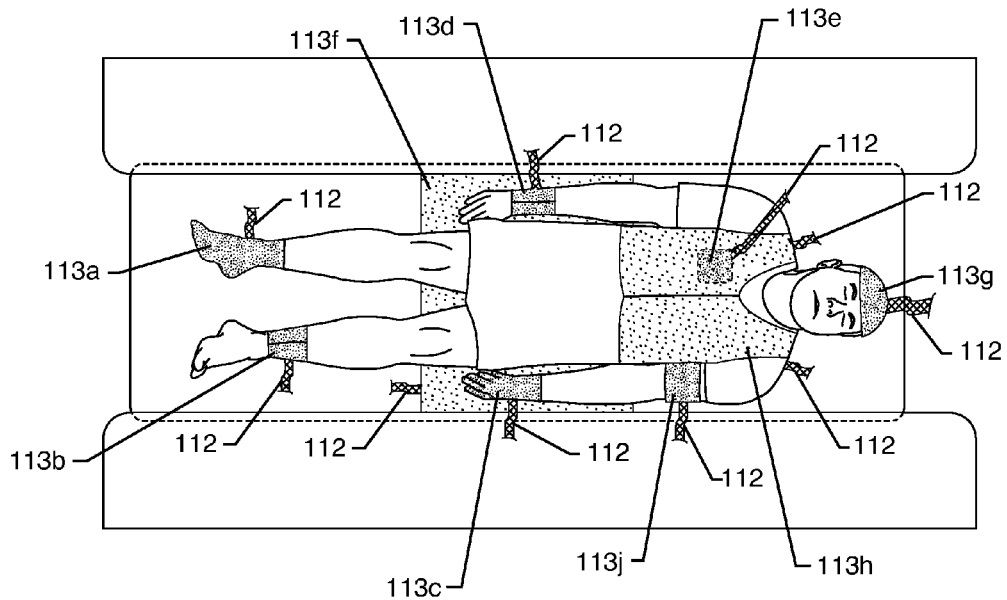
FIG. 22 is similar to FIG. 21, now showing a plurality of exemplary conductive grounding straps embodying the present invention.

FIG. 22 illustrates a number of ways to terminate the RF grounding strap 112, which is attached to the probe or catheter handle or pistol grip 110 to high surface areas of the patient's skin. In one embodiment, there is a conductive body sock or stocking 113a to which the bonding strap 112 is connected. This would divert MRI RF energies from the probe or catheter handle 110 to the surface area 113a as shown. In a preferred embodiment, there could be added Velcro closure which would terminate from the grounding strap 112 to that area. Also shown is a conductive calf/ankle bonding strap 113b. Preferably, this would be of stretchy material and can be lined in Velcro or the like, such that the conductive strap 113b fits tightly against the patient's skin. This could have an insulative material at the top (not shown). A conductive hand sock/glove is shown as 113c. A conductive forearm/wrist strap is shown as item 113d. A conductive patch electrode 113e can be stuck (below the smock) to the patient 138. This skin patch 113e could be placed in various locations. In preferred embodiments, it could be very close to the point of catheter or probe insertion. For example, patch 113e could be placed on the inside of the thigh for a femoral procedure. Conductive grounding plate or mat 113f is shown shaded underneath the patient 138. This is a conductive plate 113f onto which the patient's bare skin would be placed. For example, on the buttocks. The grounding strap 112 could extend from this grounding plate 113f in any location. The conductive headband/skull cap 113g is shown for procedures adjacent the neck or the head. A conductive compression vest is shown as 113h. A conductive arm/upper arm/bicep strap is shown as 113j.

Figure 23:
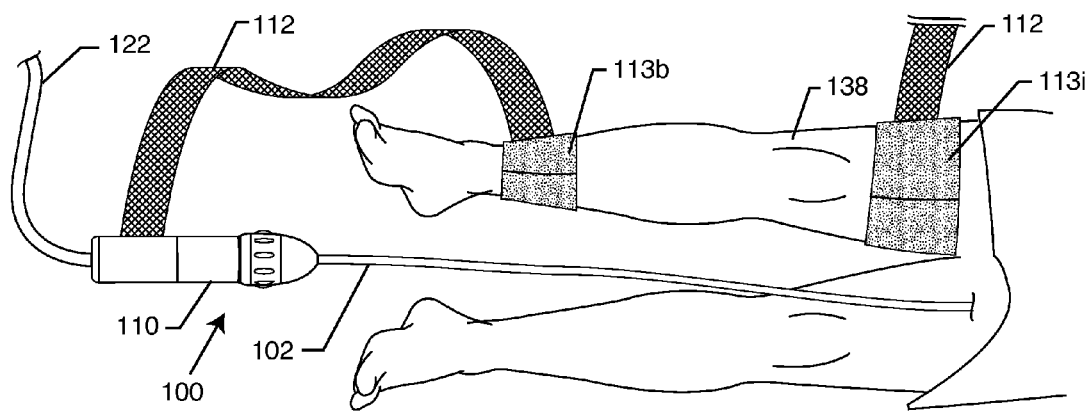
FIG. 23 is a top view of an exemplary conductive grounding strap electrically coupled between the catheter handle and the patient.

FIG. 23 is an enlarged view similar to the view of FIG. 18, now illustrating the patient 138 with the catheter body extension 102 entering through the groin area and into the femoral artery. The grounding strap 112 is electrically connected to the patient's ankle through the conductive calf/ankle strap 113b. A conductive thigh strap is shown as 113i.

Referring once again to FIG. 22, the strap 112 could also be connected to a conductive plate 113f on which the patient is resting. An optimal location for this would be close to the point of insertion of the probe or catheter into the patient's body 138. For example, in the case of a femoral insertion, a patient's buttock could be place against a metallic sheet and would present a very high RF surface area so that energy could be dissipated without undo heating. In this case, the RF bond/ground strap 112 would be located as close as possible to the probe or catheter insertion so that the length is kept relatively short thereby to minimizing its inductance or inductive reactance at high frequency.

It is well known to those skilled in the art that the inductance of any conductor relates directly to its length. In other words, keeping the RF ground strap 112 relatively short means that it will have less inductance. Less inductance means that its impedance will be lower at MRI RF-pulsed frequencies. In order to divert maximal energy to the skin contact zone, it is essential that the RF strap 112 be of low impedance. Accordingly, keeping the RF strap 112 relatively short is of paramount importance in the present invention.

One can also minimize inductance by controlling the thickness and width of the strap (wider is better). RF ground straps 112 should not only be short but also have a form factor where they are wide to minimize inductance. Flat structures such as this have much less impedance at RF frequency, such as the MRI RF pulsed frequency. As such, fabricating a strap, a plate, a patch, a pad, a mat, a wristband, an ankle band, a sock, a glove or a vest is improved as long the connecting strap 112 is relatively flat/wide as opposed to very long and thin or circular. It is also important that the contact area of the pad to the patient be of relatively large surface area and also fit snuggly or tightly against the patient's skin.

Acceptable RF ground strap 112 structures include a flat/wide braid, a fine wire braid, a coaxial braid, a woven fine wire, a dual conductor fabric, a continuous woven thread, an expandable monofilament mesh, a dissipative form metal, a flexible double-layer sheet (1 electrical and 1 thermal), a flexible braided wire, an electrically conductive tape, an anisotropic conductive film, a composite laminate, an overcoat substrate, a heat bondable conductive film, a conductive nanoparticle dispersion or any combination thereof or the like. All of the foregoing can apply to the patient pad or the RF strap 112. Furthermore, RF grounding straps 112 may comprise a braid, a mesh, a fabric, a ribbon, a rope, a woven strap, a bundled strap, a corded strap, a webbed strap and a flex strap.

RF ground strap 112 may be made from a broad family of material, such as conductive elastomers, conductive coatings, electro-conductive coatings, conductive tapes, electro-conductive tapes, conductive composites, clad sheets and metalized plastics. Specific material combinations may include copper, nickel/copper, silver/copper, carbon, titanium, stainless steel, chromium cobalt, nitinol, tantalum, tungsten, iridium, platinum, and any combinations or alloys thereof. These materials can be used to form sheets, braids, wires, coils, foils, filars, meshes, composites, powders and the like. For example, the strap 112 may comprise a copper nonwoven fabric, a nickel/copper nonwoven fabric, a nickel/copper woven fabric, a tinned copper braid, a flexible braided copper, a wide tinned flat copper braid, and so on. Additional suitable materials include gold-plated microspheres, solid particles of conductive polymers, carbon powder, carbon fibers, and intrinsically conductive polymers.

Figure 24:
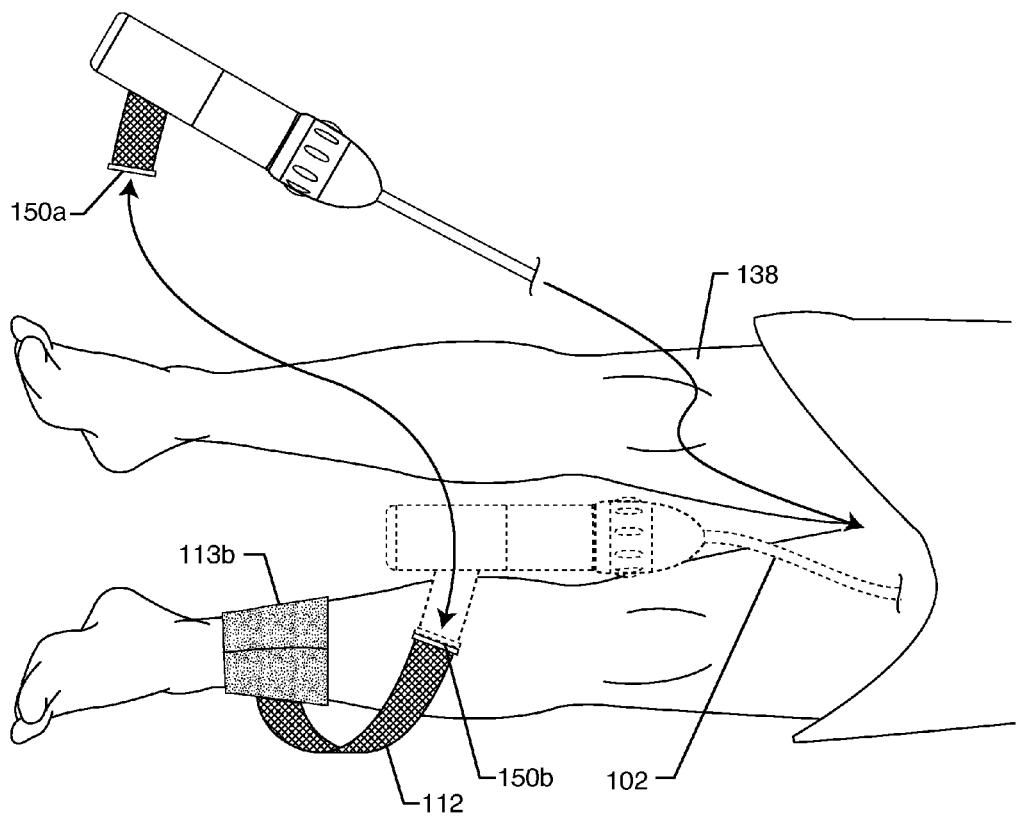
FIG. 24 is a top view similar to FIG. 19 now showing an exemplary conductive connector of the conductive grounding strap embodying the present invention.

FIG. 24 is very similar to FIG. 23 except that the RF bonding/grounding cable 112 is much closer to the point of catheter insertion. In the preferred embodiment, the conductive ankle strap 113b could be strapped at an appropriate high point on the calf to keep the length of the RF bonding/grounding strap 112 as short as possible. A novel electrical connector 150 is shown which is very important to keep the length of the strap as short as possible. When the probe or catheter 102 is just being placed, it is a fairly long distance from the point of insertion. However, once it is fully inserted, then the bond/ground strap 112 can be connected thereby keeping it as short as possible. The connector 150 electrically coupled both the sides 150a and 150b of the grounding strap 112.

Figure 25:
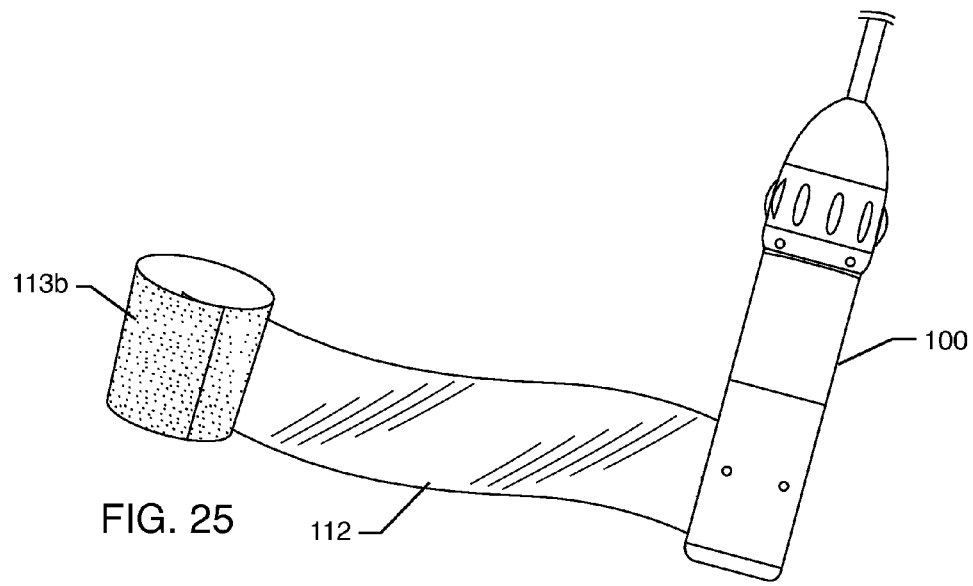
FIG. 25 is a perspective view of an exemplary probe or catheter to patient RF coupling embodying the present invention.

FIG. 25 is a perspective view of an exemplary probe or catheter to patient RF coupling embodying the present invention. The strap 112 may include a metal foil. The metal foil is flexible and of a low inductance. The strip of metal foil is substantially wide and thin. The width of the strap 112 may be half an inch, an inch, or over an inch. The strap 112 is also sufficiently flexible such that it does not interfere with a doctor's manipulation and insertion of the catheter body extension 102 when being inserted into a patient during an MRI procedure. The metal used may be copper or another low inductance metal material.

Figure 26:
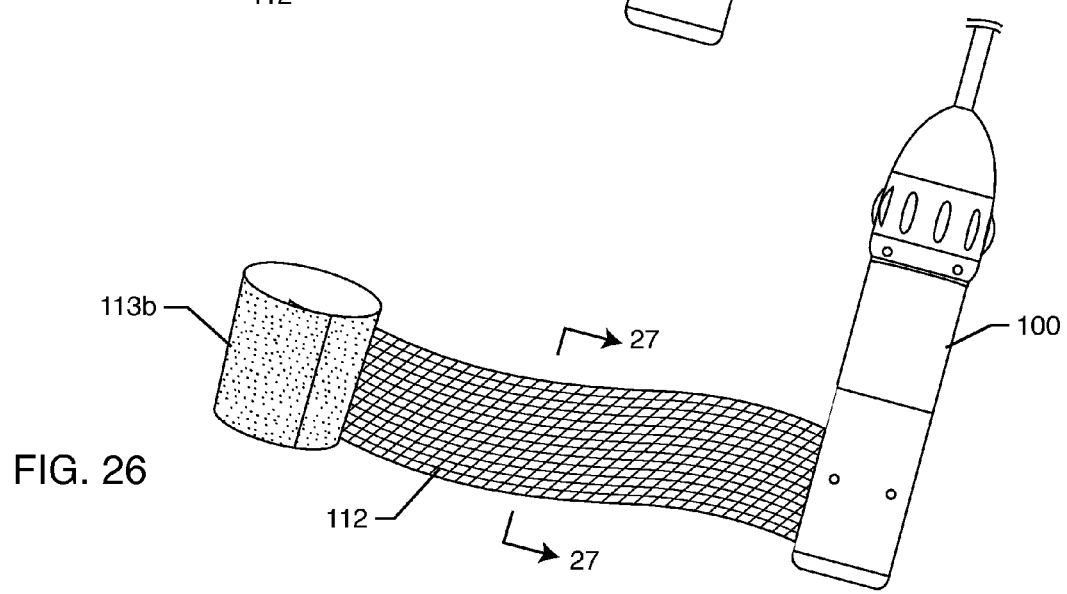
FIG. 26 is a perspective view of another exemplary probe or catheter to patient RF coupling embodying the present invention.

FIG. 26 is a perspective view of another exemplary probe or catheter to patient RF coupling embodying the present invention. Here, the strap 112 is a braided metal strap or a metal mesh strap. For instance, the braid or mesh may comprise copper. Also, the braid or metal mesh may be plated with other materials, such as tin, gold, silver, nickel or other suitable plating materials.

Figure 27:
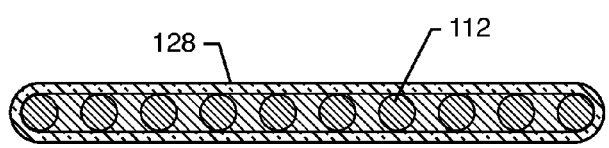
FIG. 27 is a sectional view of the structure of FIG. 26 taken along lines 27-27 showing a protective or insulative strap covering.

FIG. 27 is a sectional view of the structure of FIG. 26 taken along lines 27-27 showing a protective or insulative strap covering 128. Covering 128 may comprise a multitude of embodiments, such as flexible coverings made from plastics, composites or fabrics. The covering 128 helps to protect the strap 112 during procedures due to cleanliness issues and also to help transfer RF energy into the patient's body and not elsewhere.

In summary, the present invention describes novel probe or catheter handles which embody diverter and/or a combination of diverter and impeder elements to pull RF energy to the probe or catheter inductors during MRI scan. This energy is in turn diverted by way of an RF bonding/grounding strap from a probe or catheter handle to an energy dissipating surface which is in contact with the patient.

What is claimed is:

1. A catheter to patient RF coupling for magnetic resonance imaging, the coupling comprising:
   a) a catheter comprising a catheter housing having a nonconductive housing sidewall extending from a proximal housing end to a distal housing end, wherein the proximal housing end is connectable to a control device and the distal housing end supports a catheter body extension;
   b) a conductive interface sidewall supported by the housing, the interface sidewall comprising a first interface surface spaced from a second interface surface by an interface sidewall thickness;
   c) at least one catheter conductor extending from a distal conductor portion having a distal conductor end to a proximal conductor portion having a proximal conductor end, wherein the distal conductor portion is electrically connected to at least one distal electrode configured to be contactable with biological tissue and wherein the proximal conductor end is electrically connectable to the control device;
   d) at least one frequency selective diverter circuit comprising a first diverter circuit end spaced from a second diverter circuit end, wherein the first diverter circuit end is electrically connected to the at least one catheter conductor at a location spaced from the distal and proximal conductor ends and wherein the second diverter circuit end is electrically connected to the first interface surface; and
   e) a conductive grounding strap comprising a first strap end spaced apart from a second strap end, wherein the first strap end is configured to be permanently connected or removably connectable to the second interface surface spaced from the second diverter circuit end by the conductive interface sidewall thickness, and wherein the second strap end comprises a conductive patient interface configured to be removably connectable to a patient's skin to thereby provide a low impedance path at RF frequencies from the at least one electrode at the distal conductor portion to the diverter circuit and the conductive interface and then to the conductive grounding strap.

2. The coupling of claim 1, wherein the conductive grounding strap is selected from the group consisting of a solid metal foil strap, a braided metal strap, and a metal mesh strap.

3. The coupling of claim 2, wherein the conductive grounding strap comprises a protective or insulative covering.

4. The coupling of claim 2, wherein the metal of the solid metal foil strap, the braided metal strap and the metal mesh strap is selected from the group consisting of copper, nickel, silver, carbon, titanium, stainless steel, chromium cobalt, nitinol, tantalum, tungsten, iridium, and platinum.

5. The coupling of claim 4, wherein the conductive grounding strap further comprises a plating on the metal of the group consisting of the solid metal foil strap, the braided metal strap and the metal mesh strap, the plating selected from the group consisting of tin, gold, silver, and nickel.

6. The coupling of claim 1, wherein the conductive grounding strap comprises a flexible conductive grounding strap.

7. The coupling of claim 1, wherein the conductive grounding strap comprises a substantially flat conductive grounding strap.

8. The coupling of claim 1, wherein the conductive grounding strap is at least one-half of an inch wide.

9. The coupling of claim 1, wherein the conductive grounding strap is at least one inch wide.

10. The coupling of claim 1, wherein the second end of the conductive grounding strap is selected from the group consisting of a wrist strap, a forearm strap, an arm strap, an ankle strap, an calf strap, a thigh strap, a foot sock, a hand sock, a head band, a head cap, a glove, a sock, a patch, a table, a pad, a vest, and a gown.

11. The coupling of claim 1, wherein the catheter housing includes an insulative handle comprising a proximal handle end spaced from a distal handle end.

12. The coupling of claim 11, wherein the proximal conductor portion is at least partially disposed inside the insulative catheter handle between the proximal handle end and the distal handle end.

13. The coupling of claim 12, wherein a frequency selective impeder circuit is electrically connected in series between the at least one electrode at the distal conductor portion of the at least one catheter conductor and the at least one frequency selective diverter circuit.

14. The coupling of claim 13, wherein a second frequency selective diverter circuit is electrically coupled between the at least one catheter conductor and the first conductive interface surface.

15. The coupling of claim 14, wherein the frequency selective diverter circuit comprises a capacitor or an LC trap filter.

16. The coupling of claim 15, wherein the frequency selective impeder circuit comprises a bandstop filter or an inductor.

17. The coupling of claim 16, wherein the second frequency selective diverter circuit comprises a capacitor or an LC trap filter.

18. The coupling of claim 14 wherein, the second frequency selective diverter circuit is disposed between the frequency selective impeder circuit and the proximal end of the insulative catheter handle.

19. The coupling of claim 1, wherein a conductive connector is disposed in series along the conductive grounding strap between the first and second strap ends, wherein the conductive connector comprises a first connector end spaced from a second connector end and wherein the first and second connector ends are configured to be connected and unconnected from each other for respectively providing the conductive grounding strap as one continuous length from the first strap end to the second strap end and for separating the conductive grounding strap into two portions.

20. The coupling of claim 1, wherein a frequency selective impeder circuit is electrically in series with the at least one catheter conductor and is disposed at near or within the at least one distal electrode, and wherein the frequency selective impeder circuit comprises a bandstop filter or an inductor.

21. The coupling of claim 1 wherein the at least one frequency selective diverter circuit is disposed inside the catheter housing.

22. The coupling of claim 1 wherein the low impedance path is at MRI RF pulsed frequencies.

23. A catheter to patient RF coupling for magnetic resonance imaging, the coupling comprising:
a) a catheter comprising a catheter housing having a conductive housing sidewall comprising an outer housing surface spaced from an inner housing surface by a sidewall thickness, the housing sidewall extending from a proximal housing end to a distal housing end, wherein the proximal housing end is connectable to a control device and the distal housing end supports a catheter body extension;
b) at least one catheter conductor extending from a distal conductor portion having a distal conductor end to a proximal conductor portion having a proximal conductor end, wherein the distal conductor portion is electrically connected to at least one distal electrode configured to be contactable with biological tissue and wherein the proximal conductor end is electrically connectable to the control device;
c) at least one frequency selective diverter circuit comprising a first diverter circuit end spaced from a second diverter circuit end, wherein the first diverter circuit end is electrically connected to the at least one catheter conductor at a location spaced from the distal and proximal conductor ends and wherein the second diverter circuit end is electrically connected to the inner housing surface; and
d) a conductive grounding strap comprising a first strap end spaced apart from a second strap end, wherein the first strap end is configured to be permanently connected or removably connectable to the outer housing surface spaced from the second diverter circuit end by the conductive housing sidewall thickness, and wherein the second strap end comprises a conductive patient interface configured to be removably connectable to a patient's skin to thereby provide a low impedance path at RF frequencies from the at least one electrode at the distal conductor portion to the diverter circuit and the conductive housing and then to the conductive grounding strap.

24. The catheter of claim 23, wherein a frequency selective impeder circuit is electrically connected in series between the at least one electrode at or r the distal conductor portion of the at least one catheter conductor and the at least one frequency selective diverter circuit.

25. The catheter of claim 24, wherein a second frequency selective diverter circuit is electrically coupled between the at least one catheter conductor and the inner conductive interface surface.

26. The catheter of claim 25, wherein the frequency selective diverter circuit comprises a capacitor or an LC trap filter.

27. The catheter of claim 26, wherein the frequency selective impeder circuit comprises a bandstop filter or an inductor.

28. The catheter of claim 27, wherein the second frequency selective diverter circuit comprises a capacitor or an LC trap filter.

29. The catheter of claim 23, wherein the second strap end of the conductive grounding strap is selected from the group consisting of a wrist strap, a forearm strap, an arm strap, an ankle strap, a calf strap, a thigh strap, a foot sock, a hand sock, a head band, a head cap, a glove, a sock, a patch, a table, a pad, a vest, and a gown.

30. The catheter of claim 23, wherein a catheter body extension houses the at least one catheter conductor, the catheter body extension extending from a distal extension end to a proximal extension end, and wherein the distal extension end is at the at least one distal electrode and the proximal extension end is detachably connectable or permanently connected to the catheter handle.

31. The catheter of claim 30, wherein the at least one distal electrode comprises an ablation tip electrode.

32. The catheter of claim 31, wherein there is a first ring electrode and a second ring electrode located at or near the distal extension end of the catheter body extension.

33. The catheter of claim 31, including a frequency selective ablation tip impeder circuit disposed at, near or within the ablation tip electrode.

34. The catheter of claim 33, wherein the frequency selective ablation tip impeder circuit comprises a bandstop filter or an inductor.

35. The catheter of claim 30, wherein the distal end of the catheter body extension comprises at least one biological frequency mapping electrode.

36. The catheter of claim 23 wherein the outer interface surface is spaced closer to the outer housing surface than is the inner interface surface.

37. The catheter of claim 23 wherein the inner interface surface is spaced closer to the inner housing surface than is the outer interface Surface.

38. The catheter of claim 23 wherein the at least one frequency selective diverter circuit disposed inside the catheter housing.

39. A catheter, comprising:
a) a catheter housing extending from a proximal housing end to a distal housing end, wherein the proximal housing end is connectable to a control device and the distal housing end supports a catheter body extension;
b) at least one catheter conductor extending from a distal conductor portion having a distal conductor end to a proximal conductor portion having a proximal conductor end, wherein the distal conductor portion is electrically connected to at least one distal electrode configured to be contactable with biological tissue and wherein the proximal conductor end is electrically connectable to the control device;
c) at least one catheter body extension housing the at least one catheter conductor, the catheter body extension having an extension sidewall comprising an outer extension surface spaced from an inner extension surface by an extension sidewall thickness, wherein the extension sidewall extends from a distal extension portion having a distal extension end to a proximal extension portion having a proximal extension end, and wherein the distal extension portion is at the at least one distal electrode and the proximal extension end is detachably connectable to or permanently connected to the handle;
d) a conductive interface sidewall supported by the catheter body extension, the interface sidewall comprising a first interface surface spaced from a second interface surface by an interface sidewall thickness;
e) at least one frequency selective diverter circuit comprising a first diverter circuit end spaced from a second diverter circuit end, wherein the first diverter circuit end is electrically connected to the at least one catheter conductor at a location spaced from the distal and proximal conductor ends and wherein the second diverter circuit end is electrically connected to the first interface surface; and
f) a conductive grounding strap comprising a first strap end spaced apart from a second strap end, wherein the first strap end is configured to be permanently connected or removably connectable to the second interface surface spaced from the second diverter circuit end by the conductive interface sidewall thickness, and wherein the second strap end comprises a conductive patient interface configured to be removably connectable to a patient's skin to thereby provide a low impedance path at RF frequencies from the at least one electrode at the distal conductor portion to the diverter circuit and the conductive housing and then to the conductive grounding strap.

40. The catheter of claim 39, wherein the frequency selective diverter element comprises a capacitor or an LC trap filter.

41. The catheter of claim 39, wherein a frequency selective impeder element is electrically connected in series between the at least one electrode at the distal conductor portion of the at least one catheter conductor and the at least one frequency selective diverter element.

42. The catheter of claim 41, wherein the frequency selective impeder element comprises a bandstop filter or at least one inductor, and wherein the bandstop filter is located at, near or within the at least one distal electrode.

43. The catheter of claim 39, wherein a conductive connector is disposed in series along the conductive grounding strap between the first and second strap ends of the conductive grounding strap, wherein the conductive connector comprises a first connector end spaced from a second connector end and wherein the first and second connector ends are configured to be connected and unconnected from each other for respectively providing the conductive grounding strap as one continuous length from the first strap end to the second strap end and for separating the conductive grounding strap into two portions.

44. The coupling of claim 39, wherein a frequency selective impeder circuit is electrically in series with the at least one catheter conductor and is disposed at or near a distal end of the at least one catheter body conductor, and wherein the frequency selective impeder circuit comprises a bandstop filter or an inductor.

* * * * *

UNITED STATES PATENT AND TRADEMARK OFFICE
CERTIFICATE OF CORRECTION

PATENT NO. : 8,882,763 B2
APPLICATION NO. : 13/535029
DATED : November 11, 2014
INVENTOR(S) : Robert A. Stevenson and Christina A. Frysz It is certified that error appears in the above-identified patent and that said Letters Patent is hereby corrected as shown below:

In the claims

Column 14, line 13 after the words "disposed at" insert a --,--

Column 14, line 61 after the word "at" delete "or r"

Column 13, line 38 delete "an" and insert --a--

Column 15, line 42 after the word "circuit" insert --is--

Signed and Sealed this
Tenth Day of May, 2016

Michelle K. Lee
*Director of the United States Patent and Trademark Office*